(12) United States Patent
Masuyama et al.

(10) Patent No.: US 9,134,607 B2
(45) Date of Patent: Sep. 15, 2015

(54) PHOTORESIST COMPOSITION AND METHOD FOR PRODUCING PHOTORESIST PATTERN

(71) Applicant: SUMITOMO CHEMICAL COMPANY, LIMITED, Tokyo (JP)

(72) Inventors: Tatsuro Masuyama, Osaka (JP); Satoshi Yamaguchi, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/941,641

(22) Filed: Jul. 15, 2013

(65) Prior Publication Data
US 2014/0023971 A1 Jan. 23, 2014

(30) Foreign Application Priority Data
Jul. 18, 2012 (JP) ................. 2012-159646

(51) Int. Cl.
G03F 7/004 (2006.01)
G03F 7/38 (2006.01)
C07C 303/32 (2006.01)
C07C 309/04 (2006.01)
C07C 309/06 (2006.01)
C07C 309/12 (2006.01)
G03F 7/039 (2006.01)

(52) U.S. Cl.
CPC ............ *G03F 7/0045* (2013.01); *G03F 7/0392* (2013.01); *G03F 7/0397* (2013.01); *C07C 303/32* (2013.01); *C07C 309/04* (2013.01); *C07C 309/06* (2013.01); *C07C 309/12* (2013.01)

(58) Field of Classification Search
CPC ....... G03F 7/0397; G03F 7/0045; G03F 7/38; C07C 303/32; C07C 309/04; C07C 309/06; C07C 309/12
USPC .............. 430/270.1, 910, 921, 922, 326, 330, 430/907
See application file for complete search history.

(56) References Cited

U.S. PATENT DOCUMENTS

| | | | |
|---|---|---|---|
| 2008/0124656 A1* | 5/2008 | Kobayashi et al. | 430/286.1 |
| 2008/0318171 A1 | 12/2008 | Tsubaki | |
| 2009/0317745 A1* | 12/2009 | Mimura et al. | 430/281.1 |
| 2011/0294069 A1* | 12/2011 | Bae et al. | 430/283.1 |
| 2013/0295505 A1* | 11/2013 | Maruyama | 430/270.1 |
| 2013/0295506 A1* | 11/2013 | Sakakibara et al. | 430/270.1 |

FOREIGN PATENT DOCUMENTS

| | | |
|---|---|---|
| JP | 2003-262952 A | 9/2003 |
| JP | 2008-107806 A | 5/2008 |
| JP | 2010-164958 A | 7/2010 |

OTHER PUBLICATIONS

Tarutani, "Negative developing process and materials for resist", Monthly Display, Jun. 2011, pp. 31-37.

* cited by examiner

*Primary Examiner* — John Chu
(74) *Attorney, Agent, or Firm* — Birch, Stewart, Kolasch & Birch, LLP

(57) ABSTRACT

A photoresist composition comprising
a resin which comprises a structural unit represented by formula (I);

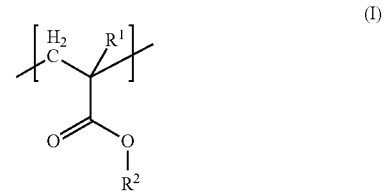

wherein $R^1$ represents a hydrogen atom or a methyl group, and
$R^2$ represents C1-C10 hydrocarbon group; and
a resin which comprises a structural unit having an acid-labile group and no structural unit represented by formula (I); and
an acid generator represented by formula (II):

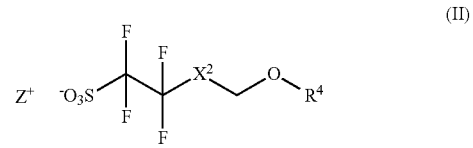

wherein $X^2$ represents a C1-C6 alkanediyl group where a hydrogen atom can be replaced by a hydroxyl group or a group —O—$R^5$ and where a methylene group can be replaced by an oxygen atom or a carbonyl group,
$R^4$ and $R^5$ each independently represent a C1-C24 hydrocarbon group where a hydrogen atom can be replaced by a fluorine atom or a hydroxyl group and where a methylene group can be replaced by an oxygen atom or a carbonyl group, and
$Z^+$ represents an organic cation.

6 Claims, No Drawings

PHOTORESIST COMPOSITION AND METHOD FOR PRODUCING PHOTORESIST PATTERN

This nonprovisional application claims priority under 35 U.S.C. §119(a) on Patent Application No. 2012-159646 filed in JAPAN on Jul. 18, 2012, the entire contents of which are hereby incorporated by reference.

FIELD OF THE INVENTION

The present invention relates to a photoresist composition and a method for producing a photoresist pattern.

BACKGROUND OF THE INVENTION

As a method for forming a negative photoresist pattern, JP2008-309879A1 mentions a photoresist composition comprising: a resin which increases in its polarity by action of an acid and which shows increased solubility in positive developer and decreased solubility in negative developer by irritation of active light or radiant lay, a compound which generates an acid by irritation of active light or radiant lay, solvent, and a resin which comprises at least one of a fluorine atom and a silicone atom.

"Monthly Display", June, 2011, page 31, published by Techno Times Co., Ltd., teaches that development with positive developer gives positive photoresist pattern, and development with negative developer gives negative photoresist pattern, in a process of forming photoresist pattern from photoresist composition by photolithography.

SUMMARY OF THE INVENTION

The present invention provides a photoresist composition suitable for producing negative photoresist pattern.

The present invention relates to the followings:

<1> A photoresist composition comprising a resin which comprises a structural unit represented by formula (i);

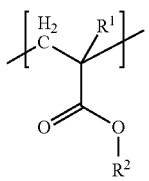

wherein $R^1$ represents a hydrogen atom or a methyl group, and $R^2$ represents a C1-C10 saturated hydrocarbon group having a fluorine atom; and a resin which comprises a structural unit having an acid-labile group and no structural unit represented by formula (I); and an acid generator represented by formula (II):

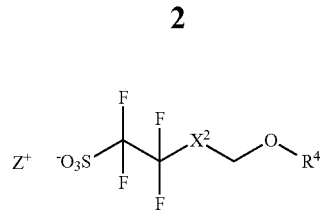

wherein $X^2$ represents a C1-C6 alkanediyl group where a hydrogen atom can be replaced by a hydroxyl group or a group —O—$R^5$ and where a methylene group can be replaced by an oxygen atom or a carbonyl group, $R^4$ and $R^5$ each independently represent a C1-C24 hydrocarbon group where a hydrogen atom can be replaced by a fluorine atom or a hydroxyl group and where a methylene group can be replaced by an oxygen atom or a carbonyl group, and $Z^+$ represents an organic cation.

<2> The photoresist composition according to <1>, wherein the acid generator is represented by formula (IIA).

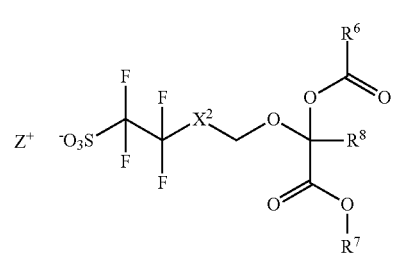

wherein $X^2$ and $Z^+$ are as defined in <1>, $R^6$ represent a C1-C17 hydrocarbon group where a hydrogen atom can be replaced by a fluorine atom or a hydroxyl group and where a methylene group can be replaced by an oxygen atom or a carbonyl group, $R^7$ represents a C1-C6 alkyl group, and $R^8$ represents a C1-C6 fluoroalkyl group, provided that the total number of carbon atoms in $R^6$, $R^7$ and $R^8$ is 19 or less.

<3> The photoresist composition according to <1> or <2>, which further comprises a salt represented by formula (B1):

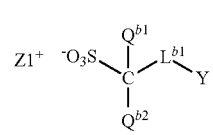

wherein $Q^{b1}$ and $Q^{b2}$ each independently represent a fluorine atom or a C1-C6 perfluoroalkyl group, $L^{b1}$ represents a single bond or a C1-C17 divalent saturated hydrocarbon group where a methylene group can be replaced by an oxygen atom or a carbonyl group, Y represents a hydrogen atom or a C3-C18 alicyclic hydrocarbon group where a methylene group can be replaced by an oxygen atom, a sulfonyl group or a carbonyl group and where a hydrogen atom can be replaced by a substituent, and $Z1^+$ represents an organic cation.

<4> The photoresist composition according to any one of <1> to <3>, which further comprises a compound represented by formula (D):

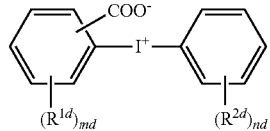

(D)

wherein $R^{1d}$ and $R^{2d}$ each independently represent a C1-C12 hydrocarbon group, a C1-C6 alkoxy group, a C2-C7 acyl group, a C2-C7 acyloxy group, a C2-C7 alkoxycarbonyl group, a nitro group or a halogen atom, and the symbols md and nd each independently represent an integer of 0 to 4.

<5> The photoresist composition according to any one of <1> to <4>, wherein the structural unit represented by formula (I) is one represented by formula (Ia);

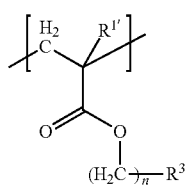

(Ia)

where $R^1$ represents a hydrogen atom or a methyl group, $R^3$ represents a C1-C4 perfluoroalkyl group, and n represents an integer of 1 to 4.

<6> The photoresist composition according to any one of <1> to <5>, which further comprises a solvent.

<7> A process for producing a photoresist pattern comprising the following steps (1) to (5):

(1) a step of applying the photoresist composition according to any one of <1> to <6> on a substrate, (2) a step of forming a composition film by drying the composition, (3) a step of exposing the composition film to radiation, (4) a step of baking the exposed composition film, and (5) a step of developing the baked composition film, thereby forming a photoresist pattern.

DESCRIPTION OF PREFERRED EMBODIMENTS

The photoresist composition of the present invention will be illustrated.

The photoresist composition of the present invention comprises a resin which comprises a structural unit represented by formula (I), which is sometimes referred to as "resin (A1)";

a resin which comprises a structural unit having an acid-labile group and no structural unit represented by formula (I), which is sometimes referred to as "resin (A2)"; and an acid generator represented by formula (II).

The resin (A1) comprises a structural unit represented by formula (I).

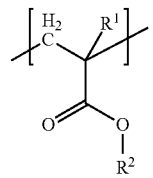

(I)

In formula (I), $R^1$ represents a hydrogen atom or a methyl group, and $R^2$ represents a C1-C10 saturated hydrocarbon group having a fluorine atom.

The saturated hydrocarbon group having a fluorine atom, which is represented by $R^2$, includes a fluorine-containing alkyl group and a fluorine-containing alicyclic hydrocarbon group.

Examples of the fluorine-containing alkyl group include difluoromethyl group, trifluoromethyl group, 1,1-difluoroethyl group, 2,2-difluoroethyl group, 2,2,2-trifluoroethyl group, perfluoroethyl group, 1,1,2,2-tetrafluoropropyl group, 1,1,2,2,3,3-hexafluoropropyl group, the 1,1,1,3,3,3-hexafluoropropan-2-yl group, perfluofoethylmethyl group, 1-(trifluoromethyl)-1,2,2,2-tetrafluoroethyl group, perfluoropropyl group, 1,1,2,2-tetrafluorobutyl group, 1,1,2,2,3,3-hexafluorobutyl group, 1,1,2,2,3,3,4,4-octafluorobutyl group, 2,2,3,3,4,4,4-heptafluorobutyl group, perfluorobutyl group, perfluoro-tert-butyl group, 2-(perfluoropropyl)ethyl group, 1,1,2,2,3,3,4,4-octafluoropentyl group, perfluoropentyl group, 1,1,2,2,3,3,4,4,5,5-decabisfluoropentyl group, 1,1-bis(trifluoromethyl)-2,2,3,3,3-pentafluoropropyl group, perfluoropentyl group, 2-(perfluorobutyl)ethyl group, 2-(perfluorooctyl)ethyl group, 1,1,2,2,3,3,4,4,5,5-decafluorohexyl group, 1,1,2,2,3,3,4,4,5,5,6,6-dodecafluohexyl groups, perfluoropentylmethyl group and perfluorohexyl group.

Examples of the fluorine-containing alicyclic hydrocarbon group include a perfluorocyclohexyl group and a perfluoroadamantyl group.

The saturated hydrocarbon group having a fluorine atom is preferably a C1-C8 fluorine-containing alkyl group, more preferably a C1-C5-fluorine-containing alkyl group. These fluorine-containing alkyl groups are preferably represented by $-(CH_2)_n-R^3$ where $R^3$ represents a C1-C4 perfluoroalkyl group and where n represents an integer of 1 to 4.

The structural unit represented by formula (I) is preferably one represented by formula (Ia).

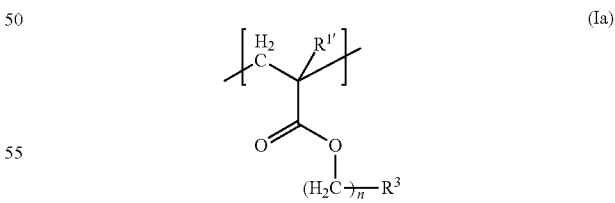

(Ia)

In formula (Ia), $R^{1'}$ represents a hydrogen atom or a methyl group, $R^3$ represents a C1-C4 perfluoroalkyl group, and n represents an integer of 1 to 4.

The perfluoroalkyl group represented by $R^3$ includes trifluoromethyl group, perfluoroethyl group, perfluoropropyl group, and perfluorobutyl group.

The structural unit represented by formula (I) is derived from a compound represented by formula (I').

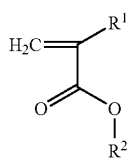
(I')

In formula (I'), $R^1$ and $R^2$ are as defined above.

The compound represented by formula (I') includes the following ones.

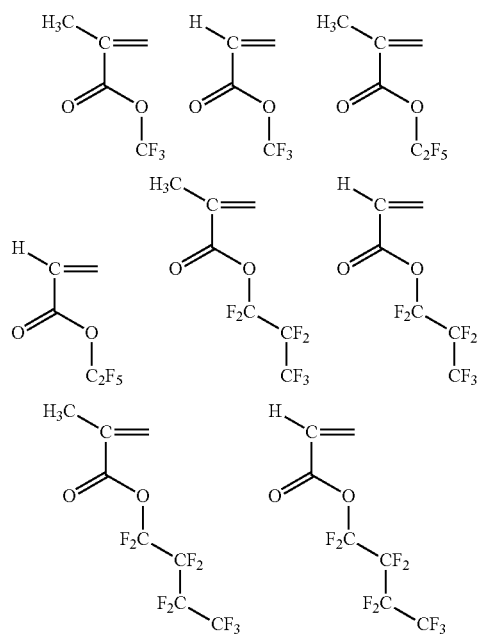

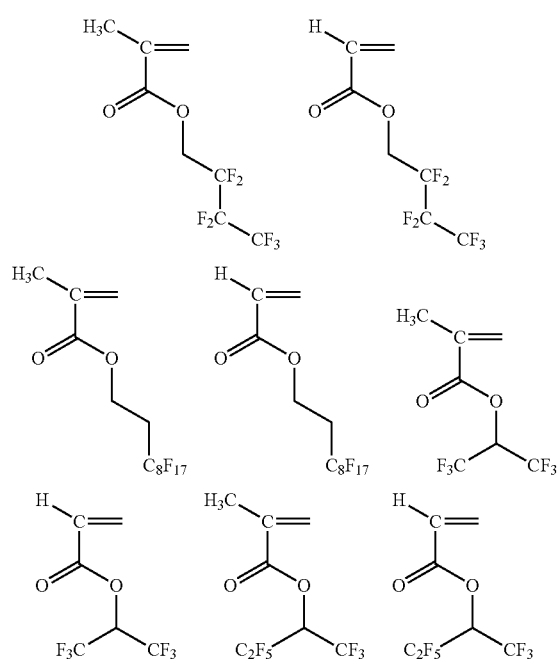

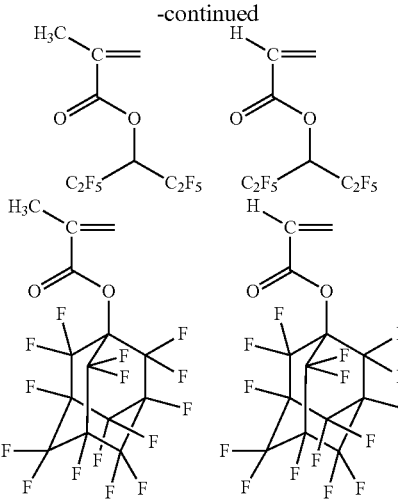

The compound represented by formula (I') can be produced by a known method such as what comprises reacting the corresponding fluoroalkyl iodine compound with (meth)acrylate in a basic condition.

The resin (A1) preferably comprises a structural unit having an acid-labile group.

Herein "an acid-labile group" means a group which comprises a leaving group capable of being cleaved in case of contacting with an acid to give a hydrophilic group such as a hydroxy group or carboxy group.

The structural unit represented by formula (I) has no acid-labile group.

Specific examples of the acid-labile group include a group represented by the formula (1):

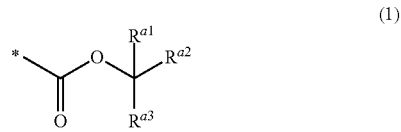

wherein $R^{a1}$, $R^{a2}$ and $R^{a3}$ each independently represent a C1-C8 alkyl group, a C3-C20 alicyclic hydrocarbon group or a combination of them, or $R^{a1}$ and $R^{a2}$ may be bonded each other to form a C2-C20 divalent hydrocarbon group, and * represents a binding position, and a group represented by the formula (2)

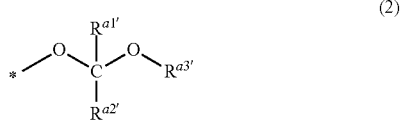

wherein $R^{a1'}$ and $R^{a2'}$ each independently represent hydrogen atom or a C1-C12 hydrocarbon group, and $R^{a3'}$ represents a C1-C20 hydrocarbon group, or $R^{a3'}$ together with $R^{a1'}$ and $R^{a2'}$ represents a C2-C20 divalent hydrocarbon group in which a methylene group of the divalent hydrocarbon group may be replaced by —O— or —S—.

Specific examples of the C1-C8 alkyl group include a methyl group, an ethyl group, a propyl group, an isopropyl group, a butyl group, a pentyl group, a hexyl group, a heptyl group and an octyl group.

The alicyclic hydrocarbon group may be monocyclic or polycyclic.

Examples of the alicyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings.

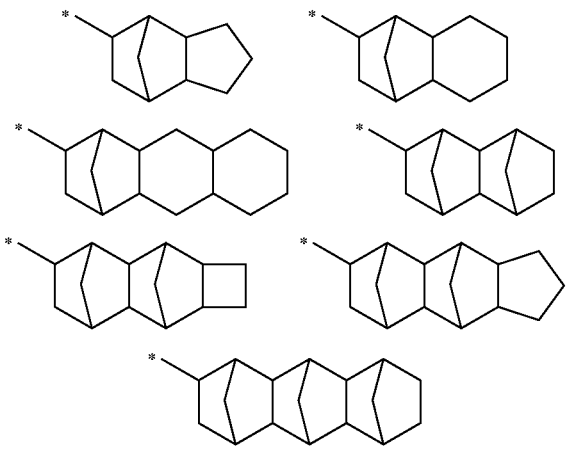

The alicyclic hydrocarbon group preferably has 3 to 16 carbon atoms.

When $R^{a1}$ and $R^{a2}$ of formula (1) are bonded each other to form a C2-C20 divalent hydrocarbon group, the moiety represented by —C($R^{a1}$)($R^{a2}$)($R^{a3}$) includes the following groups and the ring preferably has 3 to 12 carbon atoms:

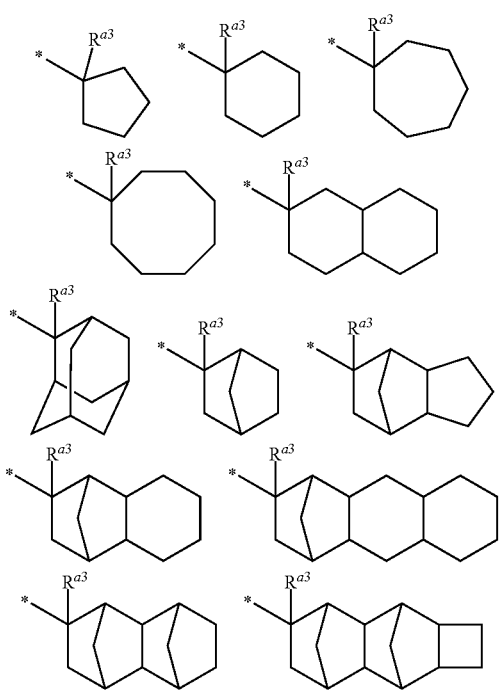

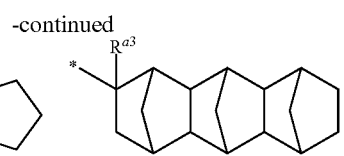

wherein $R^{a3}$ is the same as defined above and * represents a binding position to —O— of formula (1).

Preferred are the group represented by the formula (1) wherein $R^{a1}$, $R^{a2}$ and $R^{a3}$ each independently represent a C1-C8 alkyl group such as a tert-butyl group, such as 1,1'-dialkylalkoxylcarbonyl group, the group represented by the formula (1) wherein $R^{a1}$ and $R^{a2}$ are bonded each other to form an adamantyl group and $R^{a3}$ is a C1-C8 alkyl group such as a 2-alkyladaman-2-tyloxycarbonyl group, and the group represented by the formula (1) wherein $R^{a1}$ and $R^{a2}$ are C1-C8 alkyl groups and $R^{a3}$ is an adamantyl group such as a 1-(1-adaman-1-tyl)-1-alkylalkoxycarbonyl group.

As to formula (2), examples of the hydrocarbon group include an alkyl group, an alicyclic hydrocarbon group and an aromatic hydrocarbon group.

Examples of the alkyl group and the alicyclic hydrocarbon group include the same as described above. Examples of the aromatic hydrocarbon group include an aryl group such as a phenyl group, a naphthyl group, an anthryl group, a p-methylphenyl group, a p-tert-butylphenyl group, a p-adamantylphenyl group, a tolyl group, a xylyl group; a cumyl group, a mesityl group, a biphenyl group, a phenanthryl group, a 2,6-diethylphenyl group and a 2-methyl-6-ethylphenyl group.

It is preferred that at least one of $R^{a1'}$ and $R^{a2'}$ is a hydrogen atom.

Examples of the group represented by formula (2) include the following.

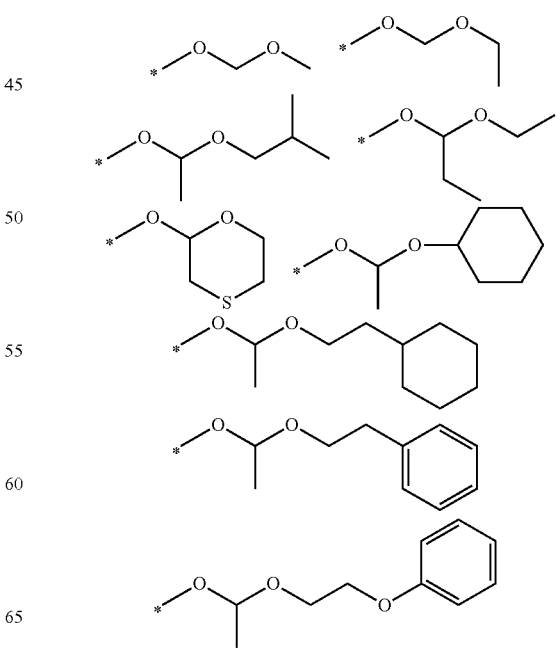

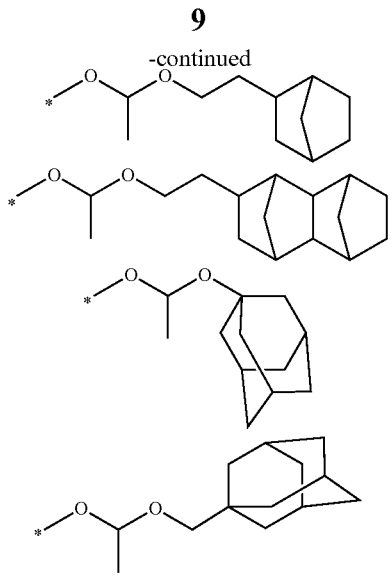

The monomer from which the structural unit having an acid-labile group is derived is preferably a compound having an acid-labile group and a carbon-carbon double bond, and is more preferably a (meth)acrylate compound having an acid-labile group.

Such (meth)acrylate compound preferably has a C5-C20 alicyclic hydrocarbon group.

When the photoresist composition comprises a resin which comprises a structural unit with a bulky structure such as a saturated alicyclic hydrocarbon group, the photoresist composition can provide a photoresist pattern with excellent resolution.

The structural unit derived from the (meth)acrylate compound having an acid-labile group includes those represented by the formulae (a1-1) and (a1-2):

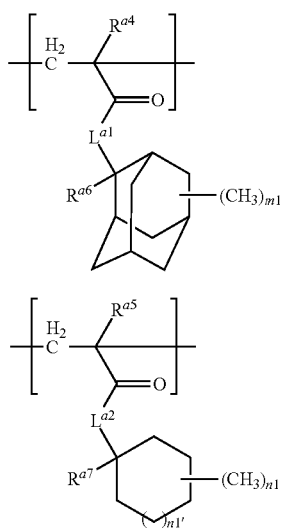

wherein $L^{a1}$ and $L^{a2}$ each independently represents an oxygen atom or *—O—$(CH_2)_{k1}$—CO—O— in which * represents a binding position to —CO—, and k1 represents an integer of 1 to 7, $R^{a4}$ and $R^{a5}$ each independently represent a hydrogen atom or a methyl group, $R^{a6}$ and $R^{a7}$ each independently represent a C1-C8 alkyl group, a C3-C18 alicyclic hydrocarbon group, and a combination of them.

m1 represents an integer of 0 to 14, n1 represents an integer of 0 to 10, and n1' represents 0 to 3.

$L^{a1}$ and $L^{a2}$ are preferably —O— or *—O—$(CH_2)_{f1}$—CO—O— in which * represents a binding position to —CO—, and f1 represents an integer of 1 to 4, and is more preferably —O—.

k1 represents preferably an integer of 1 to 4, more preferably an integer of 1.

$R^{a4}$ and $R^{a5}$ are preferably methyl groups.

Examples of the groups each represented by $R^{a6}$ and $R^{a7}$ include the same as described above.

The alkyl group represented by $R^{a6}$ and $R^{a7}$ has preferably 1 to 6 carbon atoms. The saturated cyclic hydrocarbon group represented by $R^{a6}$ and $R^{a7}$ preferably has 3 to 8 carbon atoms and more preferably 3 to 6 carbon atoms.

In the formula (a1-1), m1 is preferably an integer of 0 to 3, and is more preferably 0 or 1. In the formula (a1-2), n1 is preferably an integer of 0 to 3, and is more preferably 0 or 1, and n1' is preferably 0 or 1.

The monomer from which the structural units represented by the formula (a1-1) are derived includes compounds mentioned in JP2010-204646A1.

As the monomer from which the structural unit represented by the formula (a1-1) is derived, preferred are compounds represented by formulae (a1-1-1), (a1-1-2), (a1-1-3), (a1-1-4), (a1-1-5), (a1-1-6), (a1-1-7) and (a1-1-8), more preferred are compounds represented by formulae (a1-1-1), (a1-1-2), (a1-1-3) and (a1-1-4).

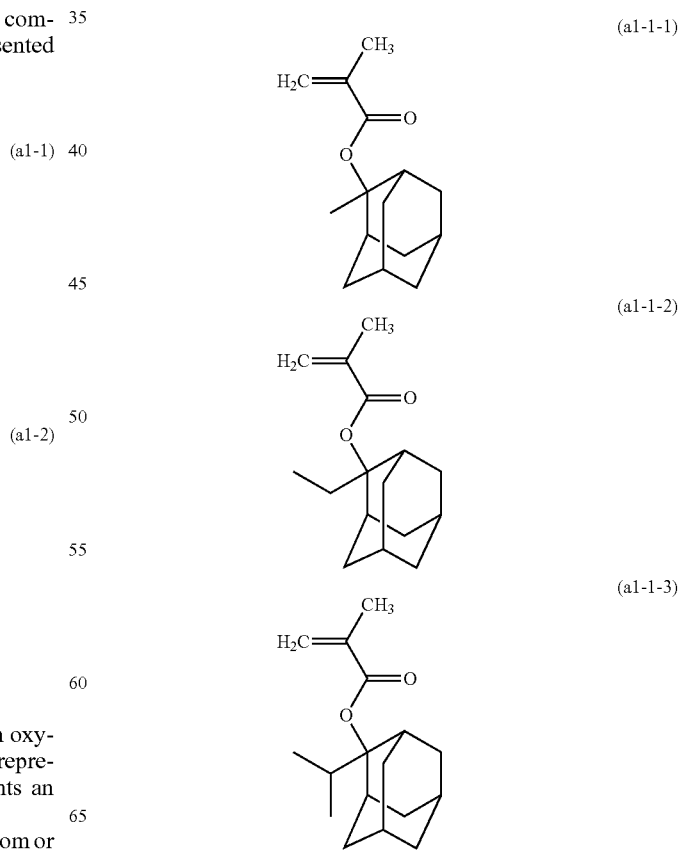

(a1-1-4)
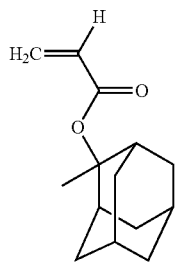

(a1-1-5)
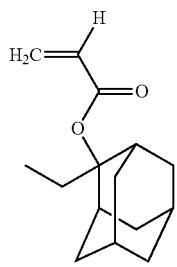

(a1-1-6)
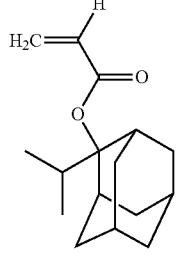

(a1-1-7)
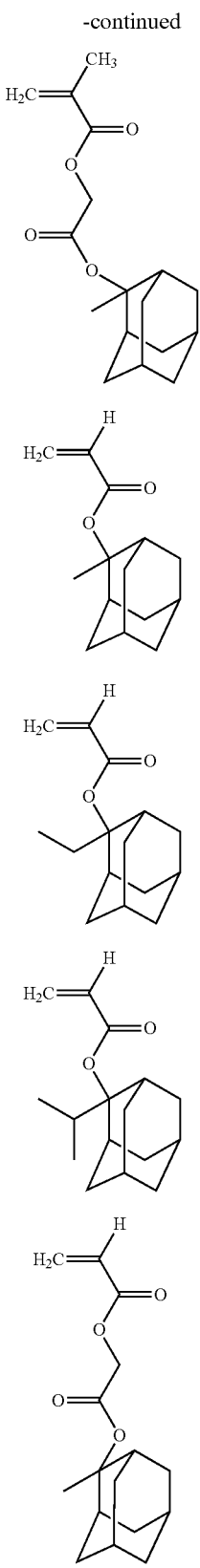

(a1-1-8)
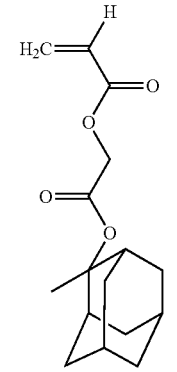

Examples of the monomer from which the structural units represented by the formula (a1-2) is derived include 1-ethyl-cyclopentant-1-yl(meth)acrylate, 1-ethyl-cyclohexan-1-yl(meth)acrylate, 1-ethyl-cyclohept-1-yl(meth)acrylate, 1-methyl-cyclopent-1-yl(meth)acrylate, 1-methyl-cyclohex-1-yl(meth)acrylate, 1-isopropyl-cyclopent-1-yl(meth)acrylate, and 1-isopropyl-cyclohex-1-yl(meth)acrylate.

As the monomer from which the structural unit represented by the formula (a1-2) is derived, preferred are those represented by formulae (a1-2-1) to (a1-2-12), more preferred are those represented by formulae (a1-2-3), (a1-2-4), (a1-2-9) and (a1-2-10), more preferred are those represented by formulae (a1-2-3) and (a1-2-9).

(a1-2-1)
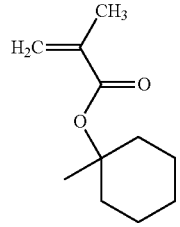

(a1-2-2)
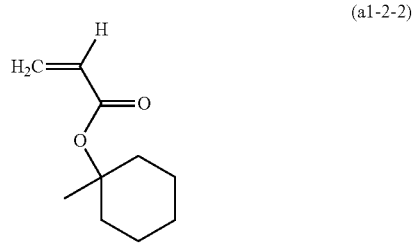

(a1-2-3)
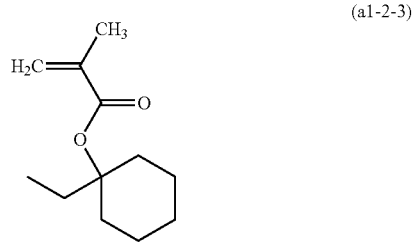

(a1-2-4)
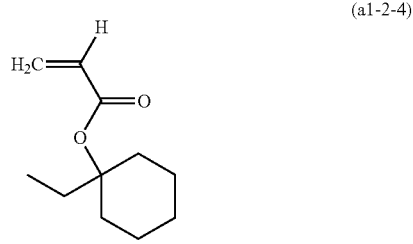

(a1-2-5)
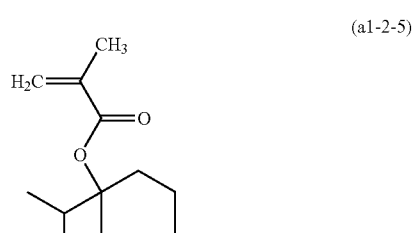

(a1-2-6) 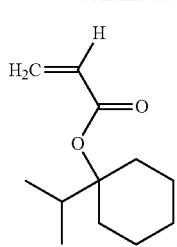

(a1-2-7) 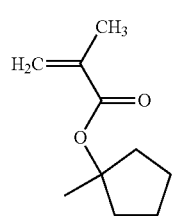

(a1-2-8) 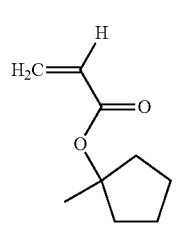

(a1-2-9) 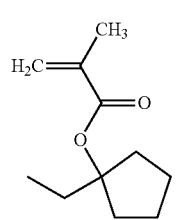

(a1-2-10) 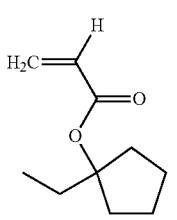

(a1-2-11) 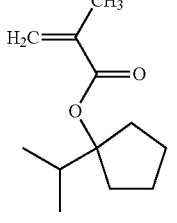

(a1-2-12) 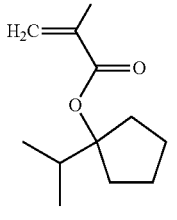

When the resin (A1) comprises at least one structural unit having an acid-labile group, the content of the structural unit in the resin is usually 10 to 95% by mole, preferably 15 to 90% by mole and more preferably 20 to 85% by mole based on all the structural units of the resin (A1).

When the resin (A1) comprises at least one structural unit represented by formula (a1-1) or formula (a1-2), the content of these structural units in the resin is usually 10 to 95% by mole, preferably 15 to 90% by mole, and more preferably 20 to 85% by mole based on all the structural units of the resin (A1).

Another example of the structural unit having an acid-labile group includes a structural unit represented by the formula (a-5);

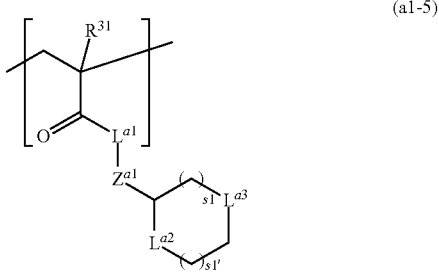

(a1-5)

wherein $R^{31}$ represents a hydrogen atom, a halogen atom, or a C1-C6 alkyl group having a halogen group, $Z^{a1}$ represents a single bond or *—O—$(CH_2)_{k4}$-$L^{a4}$-O— in which * represents a binding position to -$L^{a1}$-, and k4 represents an integer of 1 to 4, $L^{a1}$, $L^{a2}$, $L^{a3}$ and $L^{a4}$ each independently represent an oxygen atom or a sulfur atom, s1 represents an integer of 1 to 3 and s1' represents an integer of 0 to 3.

In the formula (a-5), $R^{31}$ represents preferably a hydrogen atom, a methyl group, or a trifluoromethyl group.

$L^{a1}$ preferably represents an oxygen atom.

It is preferred that one of $L^{a2}$ and $L^{a3}$ represents an oxygen atom and that the other represents a sulfur atom.

s1 preferably represents 1. s1' preferably represents an integer of 0 to 2.

$Z^{a1}$ preferably represents a single bond or —$CH_2$—CO—O—.

The monomer from which the structural unit represented by the formula (a-5) is derived includes the following ones:

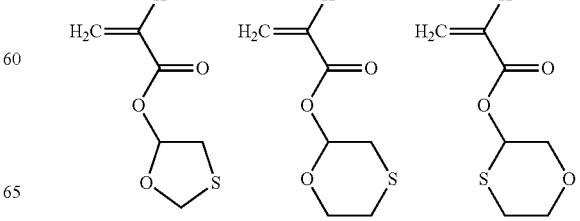

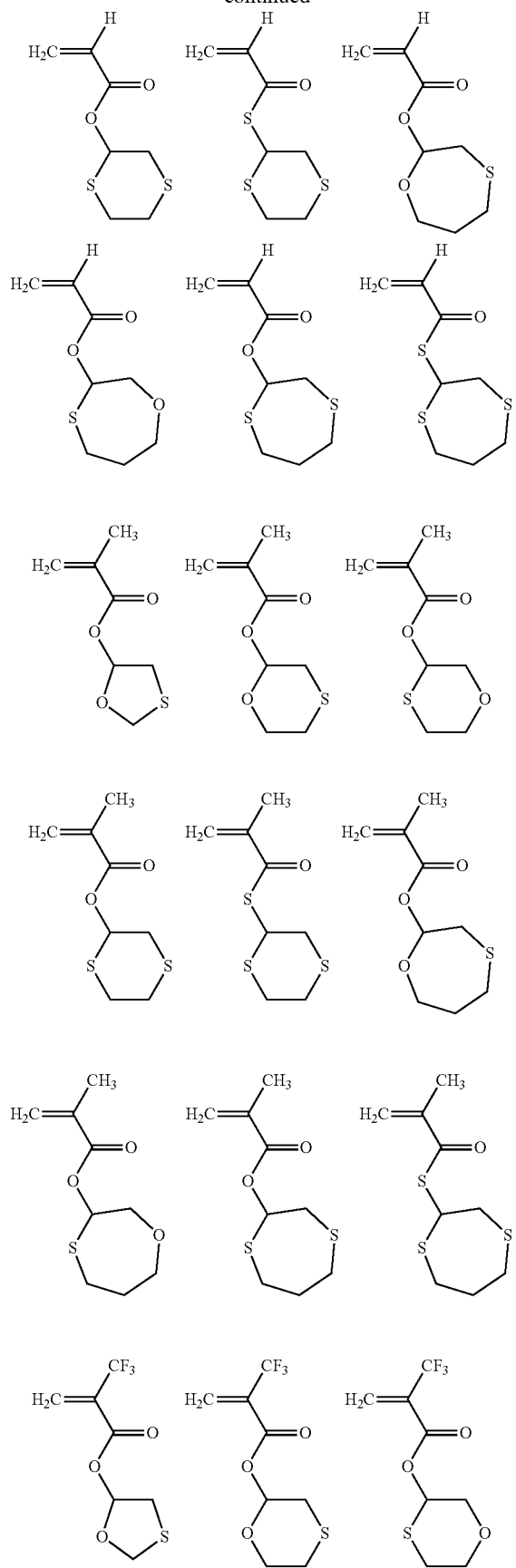
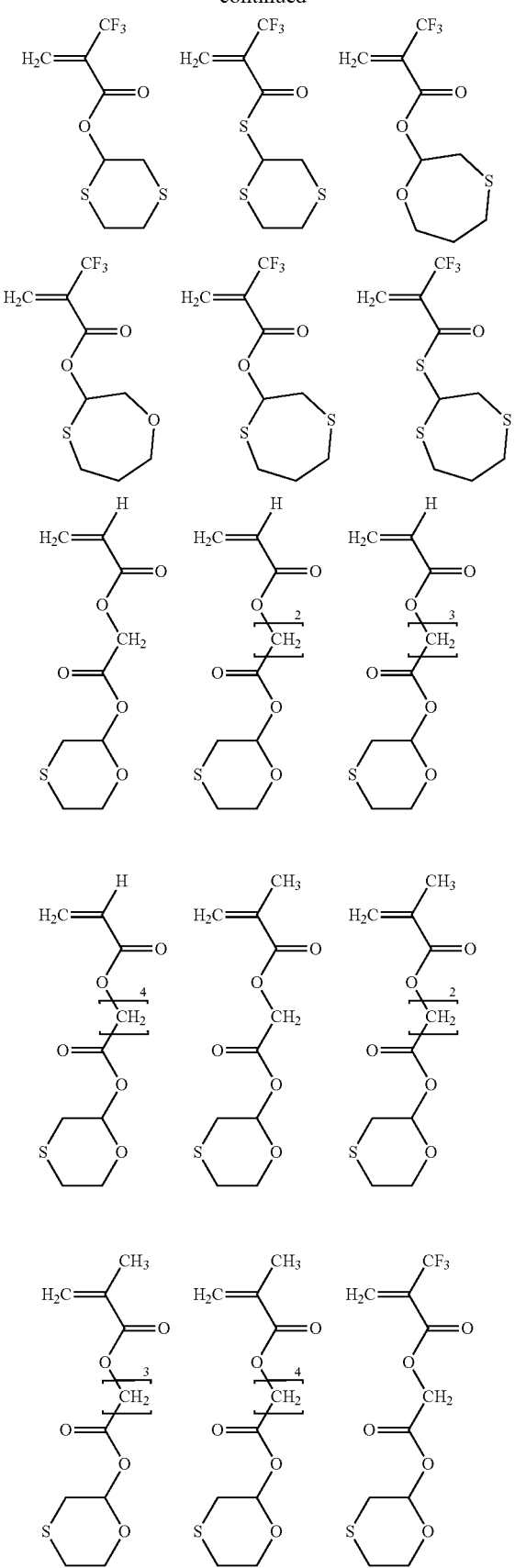

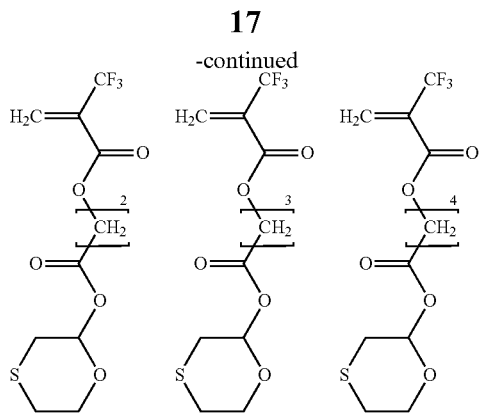

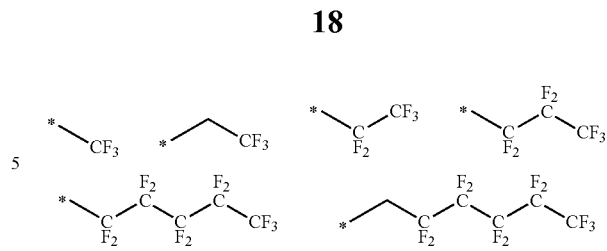

The structural unit represented by formula (IIIA) preferably includes the following ones and those in which a methyl group attached to their main chain has been replaced by a hydrogen atom.

When the resin (A1) has a structural unit derived from the compound represented by the formula (a-5), the content of the structural unit is usually 1 to 50% by mole, preferably 3 to 45% by mole and more preferably 5 to 40% by mole based on all the structural units of the resin.

The resin (A1) further comprises a structural unit having no acid-labile group other than the structural unit represented by formula (I), such as a structural unit represented by formula (IIIA), and another structural unit derived from a known monomer in the field of the art;

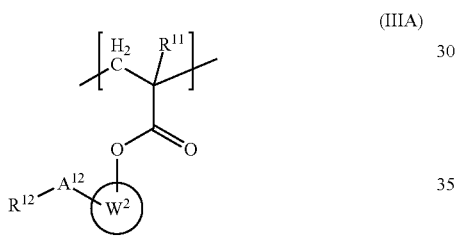
(IIIA)

wherein $R^{11}$ represents a hydrogen atom or a methyl group, ring $W^2$ represents a C1 to C10 hydrocarbon ring,
$A^{12}$ represents an oxygen atom, *—CO—O— or *—O—CO— in which * represents a binding position to ring $W^2$, and $R^{12}$ represents a C1-C6 fluorine-containing alkyl group.

The hydrocarbon ring represented by ring $W^2$ includes an alicyclic hydrocarbon ring, preferably a saturated alicyclic hydrocarbon ring.

The saturated alicyclic hydrocarbon ring includes the following ones.

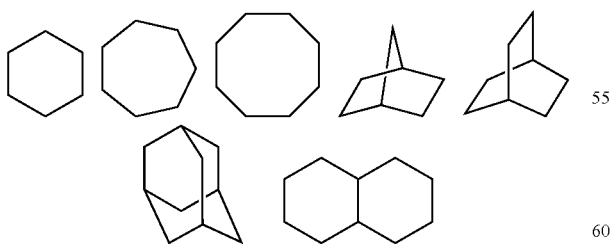

The ring $W^2$ includes an adamantane ring and a cyclohexane ring, preferably an adamantane ring.

The fluorine-containing alkyl group represented by $R^{12}$ includes those as mentioned above, preferably the following ones.

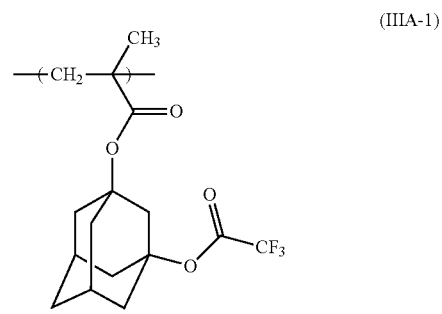
(IIIA-1)

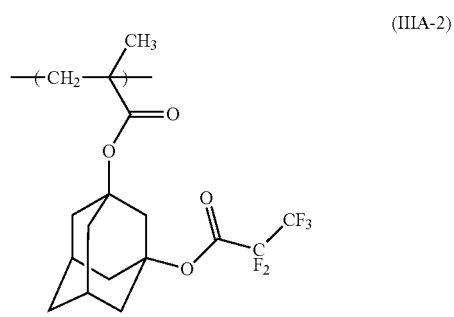
(IIIA-2)

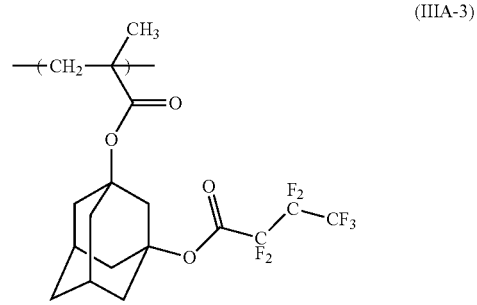
(IIIA-3)

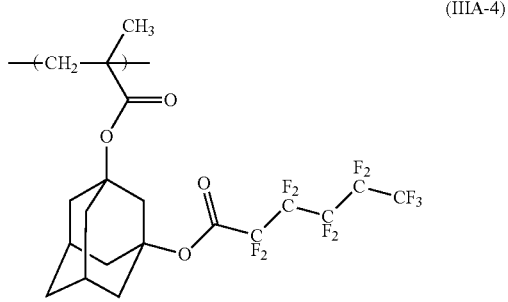
(IIIA-4)

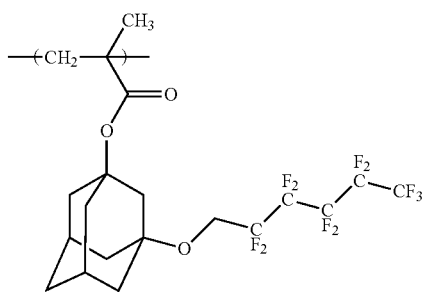
(IIIA-5)

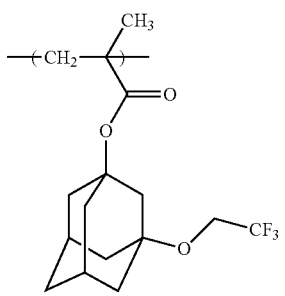
(IIIA-6)

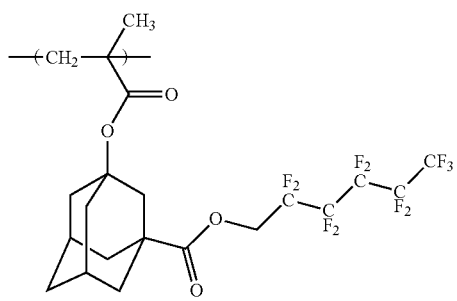
(IIIA-7)

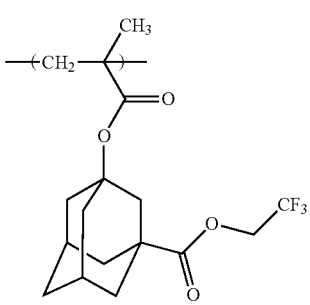
(IIIA-8)

In the resin (A1), the content of the structural unit represented by formula (I) is usually 5 to 100% by mole, preferably 20 to 100% by mole based on all the structural units of the resin.

The resin (A1) preferably comprises a structural unit represented by formula (I) and a structural unit having an acid-labile group, and more preferably consists of a structural unit represented by formula (I) and a structural unit having an acid-labile group.

The resin (A1) preferably comprises a structural unit represented by formula (a1-1) and/or formula (a1-2) as a structural unit represented having an acid-labile group.

When the resin (A1) consists of a structural unit represented by formula (I) and a structural unit having an acid-labile group, these contents are
preferably 10 to 95% by mole of the structural unit represented by formula (I) and 5 to 90% by mole of the structural unit having an acid-labile group,
more preferably 15 to 90% by mole of the structural unit represented by formula (I) and 10 to 85% by mole of the structural unit having an acid-labile group, and
still more preferably 20 to 85% by mole of the structural unit represented by formula (I) and 10 to 80% by mole of the structural unit having an acid-labile group,
based on all the structural units of the resin.

When the resin (A1) further comprises a structural unit having no acid-labile group, a structural unit represented by formula (IIIA), and another structural unit derived from a known monomer in the field of the art, the total content of these structural units is preferably 1 to 95% by mole, more preferably 2 to 80% by mole based on all the structural units of the resin.

Each structural unit may be contained singly or together with other ones represented by the same formula in the resin (A1).

The resin (A1) can be produced with a known polymerization method, such as radical polymerization, using monomers from which the structural unit represented by formula (I) and the other structural unit as mentioned above are derived.

The content of each structural unit in the resin (A1) can be controlled by controlling the amount of each monomer from which the corresponding structural unit is derived at production of the resin.

The weight average molecular weight of the resin (A1) is preferably 5000 or more, more preferably 7,000 or more, and still more preferably 10000 or more, and preferably 80,000 or less, more preferably 50,000 or less, and still more preferably 30,000 or less.

The weight-average molecular weight can be measured with gel permeation chromatography (standard: polyethylene). The detailed method of measurement is described in Examples of the present specification.

The photoresist composition of the present invention comprises the resin (A2).

The resin (A2) comprises a structural unit having an acid-labile group and no structural unit represented by formula (I).

The resin (A2) may comprise a structural unit having no acid-labile group and another structural unit derived from a known monomer in the field.

The resin (A2) preferably shows such properties that it is decomposed to increase solubility in an organic solvent such as butyl acetate and 2-heptanone by action of an acid.

When the resin (A2) comprises at least one structural unit having an acid-labile group, the content of the structural unit in the resin is usually 10 to 95% by mole, preferably 15 to 90% by mole and more preferably 20 to 85% by mole based on all the structural units of the resin (A1).

When the resin (A2) comprises at least one structural unit represented by formula (a1-1) or formula (a1-2), the content of the structural unit in the resin is usually 10 to 95% by mole, preferably 15 to 90% by mole, and more preferably 20 to 85% by mole based on all the structural units of the resin (A2).

When the resin (A2) comprises at least one structural unit represented by formula (a1-5), the content of the structural unit in the resin is usually 1 to 50% by mole, preferably 3 to 45% by mole, and more preferably 5 to 40% by mole based on all the structural units of the resin (A2).

The structural unit having no acid-labile group preferably comprises a hydroxy group or a lactone ring. When the photoresist composition comprises such a structural unit, its resolution of photoresist pattern and its adhesiveness with a substrate can be improved. These structural units can be suitably selected depending on exposure source for producing photoresist pattern from the photoresist composition.

When KrF excimer laser (wavelength: 248 nm) lithography system, or a high energy laser such as electron beam and extreme ultraviolet is used as an exposure system, preferred is a resin which comprises the structural unit having no acid-labile group but having a phenolic-hydroxy group.

When ArF excimer laser (wavelength: 193 nm) is used as an exposure system, preferred is a resin which comprises the structural unit having no acid-labile group but having an alcoholic hydroxy group, and more preferred is a resin which comprises the structural unit represented by the following formula (a2-1).

The structural unit having no acid-labile group but having a hydroxy group, preferably has a hydroxyadamantyl group.

Preferred examples of the structural unit having no acid-labile group but having a hydroxy group include a structural unit represented by the formula (a2-1):

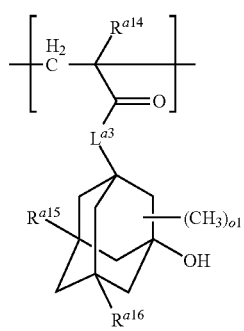

(a2-1)

wherein $R^{a14}$ represents a hydrogen atom or a methyl group, $R^{a15}$ and $R^{a16}$ each independently represent a hydrogen atom, a methyl group or a hydroxy group, $L^{a3}$ represents *—O— or *—O—$(CH_2)_{k2}$—CO—O— in which * represents a binding position to —CO—, and k2 represents an integer of 1 to 7, and of represents an integer of 0 to 10.

In the formula (a2-1), $L^{a3}$ is preferably *—O— or *—O—$(CH_2)_{f2}$—CO—O— in which * represents a binding position to —CO—, and f2 represents an integer of 1 to 4, is more preferably *—O— and *—O—$CH_2$—CO—O—, and is still more preferably *—O—.

$R^{a14}$ is preferably a methyl group.

$R^{a15}$ is preferably a hydrogen atom.

$R^{a16}$ preferably a hydrogen atom or a hydroxy group.

o1 is preferably 0, 1, 2 or 3 and is more preferably 0 or 1.

The monomer from which the structural unit represented by the formula (a2-1) is derived includes those mentioned in JP2010-204646A1, preferably those represented by formulae (a2-1-1), (a2-1-2), (a2-1-3), (a2-1-4), (a2-1-5) and (a2-1-6), and more preferably those represented by formulae (a2-1-1), (a2-1-2), (a2-1-3) and (a2-1-4), still more preferably those represented by formulae (a2-1-1) and (a2-1-3).

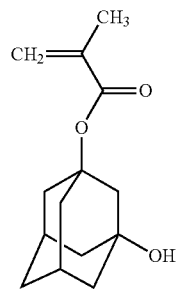

(a2-1-1)

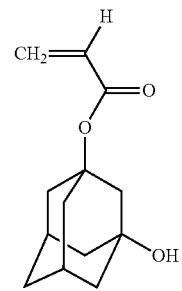

(a2-1-2)

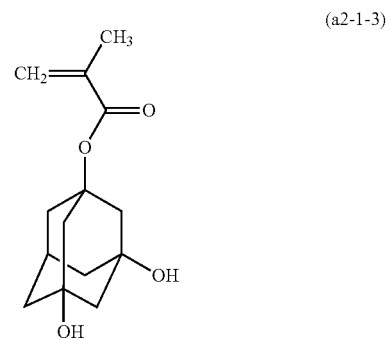

(a2-1-3)

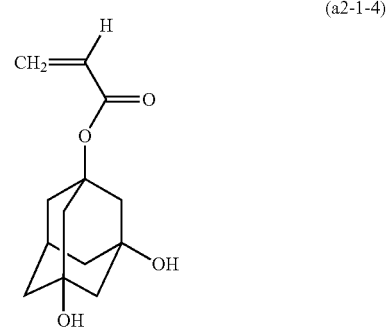

(a2-1-4)

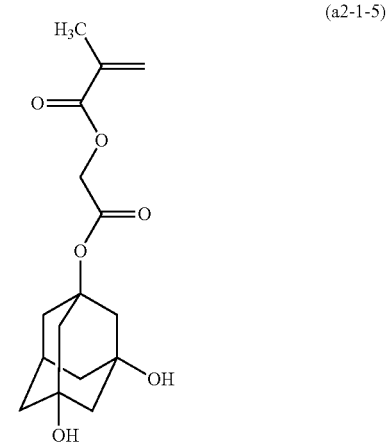 [SMILES: C=CC(=O)OCC(=O)OC12CC3CC(O)(CC(O)(C3)C1)C2]

(a2-1-5)

(a2-1-6)

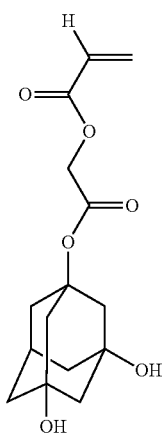

When the resin (A2) has the structural unit represented by the formula (a2-1), the content of the structural unit represented by the formula (a2-1) is usually 1 to 45% by mole and preferably 1 to 40% by mole, more preferably 1 to 35% by mole, still more preferably 2 to 20% by mole, based on total molar of all the structural units of the resin.

As to the structural unit having no acid-labile group but having a lactone ring, examples of the lactone ring include a monocyclic lactone ring such as β-propiolactone ring, γ-butyrolactone ring and δ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit having no acid-labile group but having a lactone ring include those represented by the formulae (a3-1), (a3-2) and (a3-3):

(a3-1)

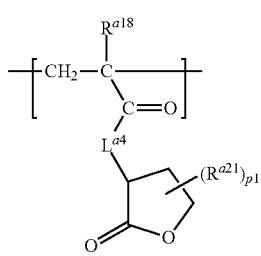

(a3-2)

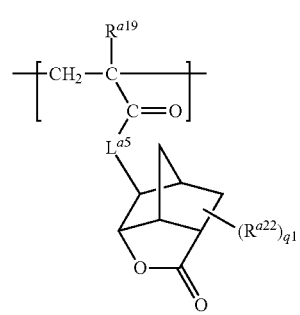

(a3-3)

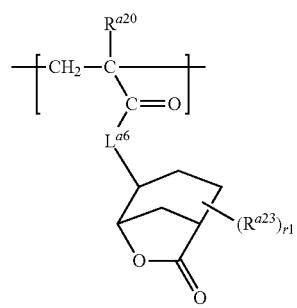

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each independently represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— and *—O—$CH_2$—CO—O—, and it is still more preferred that $L^{a4}$, $L^{a5}$ and $L^{a6}$ are *—O—.

$R^{a18}$, $R^{a19}$, $R^{a20}$ and $R^{a21}$ are preferably methyl groups.

It is preferred that $R^{a22}$ and $R^{a23}$ are independently in each occurrence a carboxyl group, a cyano group or a methyl group.

It is preferred that p1, q1 and r1 are an integer of 0 to 2, and it is more preferred that p1, q1 and r1 are 0 or 1.

Monomers from which the structural units having no acid-labile group but having a lactone ring are derived are mentioned in JP2010-204646A1. Examples of monomers from which the structural unit having no acid-labile group but having a lactone ring include preferably those represented by the formulae (a3-1-1), (a3-1-2), (a3-1-3) and (a3-1-4), the formulae (a3-2-1), (a3-2-2), (a3-2-3) and (a3-2-4), and the formulae (a3-3-1), (a3-3-2), (a3-3-3) and (a3-3-4), and more preferably those represented by the formulae (a3-1-1) and (a3-1-2), and the formulae (a3-2-3) and (a3-2-4), still more preferably those represented by the formulae (a3-1-1) and (a3-2-3).

(a3-1-1)

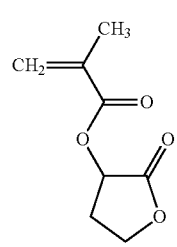

(a3-1-2)
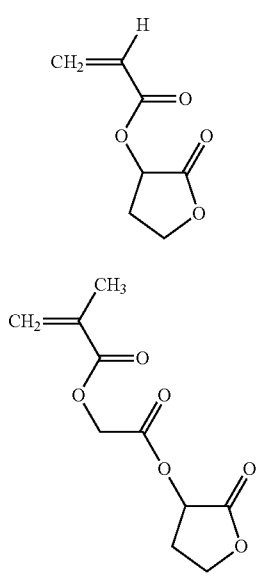
(a3-1-3)
(a3-1-4)
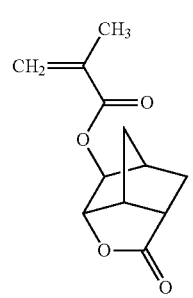
(a3-2-1)
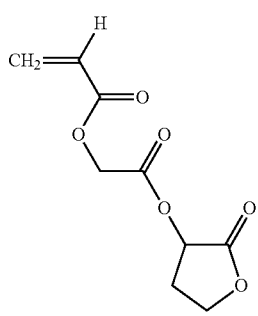
(a3-2-2)
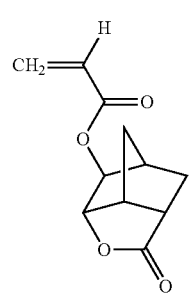
(a3-2-3)
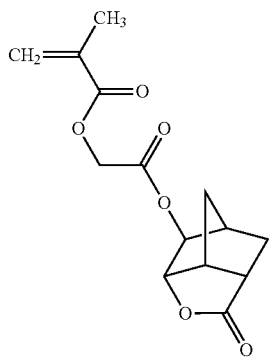
(a3-2-4)
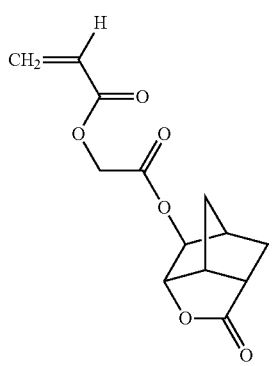
(a3-3-1)
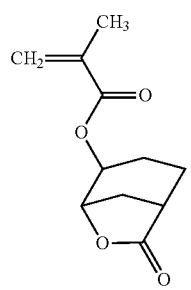
(a3-3-2)
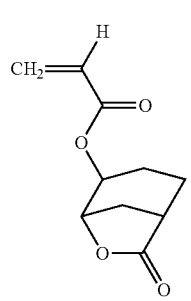
(a3-3-3)
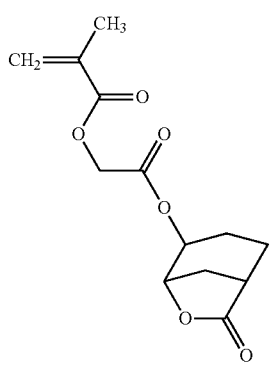

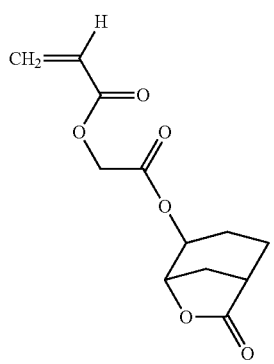

(a3-3-4)

The content of the structural unit having no acid-labile group but having a lactone ring is usually 5 to 70% by mole, preferably 10 to 60% by mole, and more preferably 10 to 65% by mole based on the total molar of the structural units in the resin (A2).

The resin (A2) comprises a structural unit having an acid-labile group and a structural unit having no acid-labile group.

In the resin (A2), the structural unit having an acid-labile group is preferably those represented by formulae (a1-1) and (a1-2), more preferably those represented by formula (a1-1). The structural unit having no acid-labile group is preferably those having a hydroxyl group or a lactone ring. For the resin (A2), the structural unit having no acid-labile group but having a hydroxyl group is preferably those represented by formula (a2-1). For the resin (A2), the structural unit having no acid-labile group but having a lactone ring is preferably those represented by formulae (a3-1) and (a3-2).

When the resin (A2) comprises a structural unit derived from a monomer having an adamantyl group, preferably the structural unit represented by formula (a1-1), the content of the structural unit is preferably 15% or more by mole based on 100% by mole of all of the structural units having an acid-labile group. When the photoresist composition comprises adamantane ring-containing structural units in larger amount, the photoresist pattern obtained therefrom can have more improved resistance to dry-etching.

The content of the structural unit having an acid-labile group in the resin (A2) is usually 1 to 100% by mole, preferably 10 to 95% by mole, more preferably 15 to 90% by mole, and still more preferably 20 to 85% by mole, based on all the structural units of the resin.

When the resin (A2) comprises a structural unit having no acid-labile group, the contents of the structural unit is usually 5 to 95% by mole, preferably 10 to 80% by mole, more preferably 20 to 70% by mole, and still more preferably 30 to 70% by mole, based on all the structural units of the resin.

When the resin (A2) comprises a structural unit having an acid-labile group and a structural unit having no acid-labile group, the contents of these structural units are
preferably 10 to 95% by mole of the structural unit having an acid-labile group and 5 to 90% by mole of the structural unit having no acid-labile group,
more preferably 15 to 90% by mole of the structural unit having an acid-labile group and 10 to 85% by mole of the structural unit having no acid-labile group, and
still more preferably 20 to 85% by mole of the structural unit having an acid-labile group and 15 to 80% by mole of the structural unit having no acid-labile group,
based on all the structural units of the resin.

The weight-average molecular weight of the resin (A2) is usually 2,500 or more, preferably 3,000 or more, more preferably 4,000 or more, and usually 50,000 or less, preferably 30,000 or less, more preferably 15,000 or less.

The photoresist composition of the present invention comprises the resin (A1) and the resin (A2) in an amount of from usually 0.01:10 to 5:10, preferably from 0.05:10 to 3:10, more preferably from 0.1:10 to 2:10, and still more preferably from 0.2:10 to 1:10, represented by [the content of resin (A1)]:[the content of resin (A2)] basis on weight.

The photoresist composition of the present invention may further comprise another resin than the resin (A1) and the resin (A2). Such another resin includes what consists of the structural units having no acid-labile group as mentioned above and no structural unit represented by formula (I).

When the photoresist composition comprises such another resin, the contents of the resin are preferably 0.1 to 50% by mole, more preferably 0.5 to 30% by mole, still more preferably 1 to 20% by mole of the total resins in the photoresist composition.

The photoresist composition of the present invention usually contains 80% by weight or more of the resins based on sum of solid component. The photoresist composition of the present invention usually comprises 99.9% by mass or less of the resins based on sum of solid component. In this specification, "solid component" means components other than solvent in the photoresist composition. The content can be measured with a known analysis equipment such as gas or liquid chromatography.

The photoresist composition of the present invention comprises a salt represented by the formula (II).

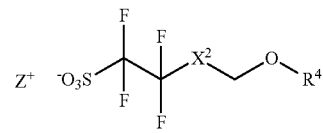

(II)

In the formula, $X^2$ represents a C1-C6 alkanediyl group where a hydrogen atom can be replaced by a hydroxyl group or a group —O—$R^5$ and where a methylene group can be replaced by an oxygen atom or a carbonyl group,
$R^4$ and $R^5$ each independently represent a C1-C24 hydrocarbon group where a hydrogen atom can be replaced by a fluorine atom or a hydroxyl group and where a methylene group can be replaced by an oxygen atom or a carbonyl group, and
$Z^+$ represents an organic cation.

The alkanediyl group represented by $X^2$ includes a methylene group, an ethylene group, a propane-1,3-diyl group, a propane-1,2-diyl group, a butane-1,4-diyl group, a pentane-1,5-diyl group, a hexane-1,6-diyl group, an etane-1,1-diyl group, a propane-1,1-diyl group, a propane-2,2-diyl group, a butane-1,3-diyl group, 2-methylpropane-1,2-diyl group, a pentane-1,4-diyl group and 2-methylbutane-1,4-diyl group. The alkanediyl group is preferably a methylene group.

The alkanediyl group where a methylene group has been replaced by an oxygen atom or a carbonyl group includes the following divalent groups;

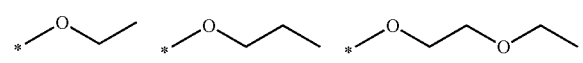

-continued where * represents a binding position to CF$_2$.

The alkanediyl group where a hydrogen atom can be replaced by a hydroxyl group or a group —O—R$^5$ and where a methylene group can be replaced by an oxygen atom or a carbonyl group includes the following divalent group;

where * represents a binding position to CF$_2$.

The hydrocarbon group represented by R$^4$ and R$^5$ may be saturated or unsaturated one, which includes a linear chain alkyl or alkenyl group, a branched chain alkyl or alkenyl group, a monocyclic or polycyclic alicyclic hydrocarbon group, an aromatic hydrocarbon group, and a group comprising two or more of them.

The linear chain alkyl group includes a methyl group, an ethyl group, a propyl group, a butyl group, a pentyl group and a hexyl group.

The branched chain alkyl group includes an isopropyl group, a butyl group, an isobutyl group, a sec-butyl group and a tert-butyl group. The linear or branched chain alkenyl group includes a vinyl group and α-methylvinyl group.

The monocyclic alicyclic hydrocarbon group includes a cyclobutyl group, a cyclopenyl group, a cyclohexyl group and a cyclooctyl group.

The polycyclic alicyclic group includes a norbornyl group and an adamantyl group.

The aromatic hydrocarbon group includes phenyl group, naphthyl group, p-methylphenyl group, p-tert-butylphenyl group, p-adamantylphenyl group, tolyl group, xylyl group, 2,6-diethylphenyl group, 2-methyl-6-ethylphenyl group.

The salt represented by the formula (II) is preferably one represented by formula (IIA).

(IIA)

In the formula, X$^2$ and are as defined above.

R$^6$ represents a C1-C17 hydrocarbon group where a hydrogen atom can be replaced by a fluorine atom or a hydroxyl group and where a methylene group can be replaced by an oxygen atom or a carbonyl group, R$^7$ represents a C1-C6 alkyl group, and R$^8$ represents a C1-C6 fluoroalkyl group, provided that the total carbon number of R$^6$, R$^7$ and R$^8$ is 19 or less.

Examples of the hydrocarbon group represented by R$^6$ include C1-C17 hydrocarbon groups among the above-mentioned examples for R$^4$, specifically a C1-C17 alkyl or alkenyl group, C3-C17 monocyclic or polycyclic alicyclic hydrocarbon group, and C6-C17 aromatic hydrocarbon group and combination of them.

The hydrocarbon group represented by R$^6$ includes a C1-C17 alicyclic hydrocarbon group where a methylene group can be replaced by an oxygen atom or a carbonyl group.

The alicyclic hydrocarbon group where a methylene group has been replaced by an oxygen atom or a carbonyl group includes the following ones:

where * represents a binding position.

The alkyl group represented by R$^7$ includes a methyl group, an ethyl group, a propyl group, a butyl group, a pentyl group and a hexyl group.

The fluoroalkyl group represented by R$^8$ includes a trifluoromethyl group, a perfluoroethyl group, a 1,1,2,2-tetrafluoroethyl group, a perfluorobutyl group, a 1,1,2,2,3,3,4,4-octafluoroethyl group, preferably a trifluoromethyl group.

R$^6$ preferably represents a C1-C4 alkyl group such as a methyl group, an ethyl group; a C2-C4 alkylene group such as an ethylene group, propylene group; a phenyl group; a C3-C10 alicyclic hydrocarbon group where a methylene group can be replaced by carbonyl group and where a hydrogen atom can be replaced by a hydroxy group, such as a cyclohexyl group, an adamantyl group, oxoadamantyl group, and hydroxyadamantyl group.

R$^7$ represents preferably a C1-C2 alkyl group, more preferably ethyle group.

R$^8$ represents preferably a C1-C3 fluoroalkyl group, more preferably a trifluoromethyl group.

The salt represented by the formula (II) is preferably the following ones.

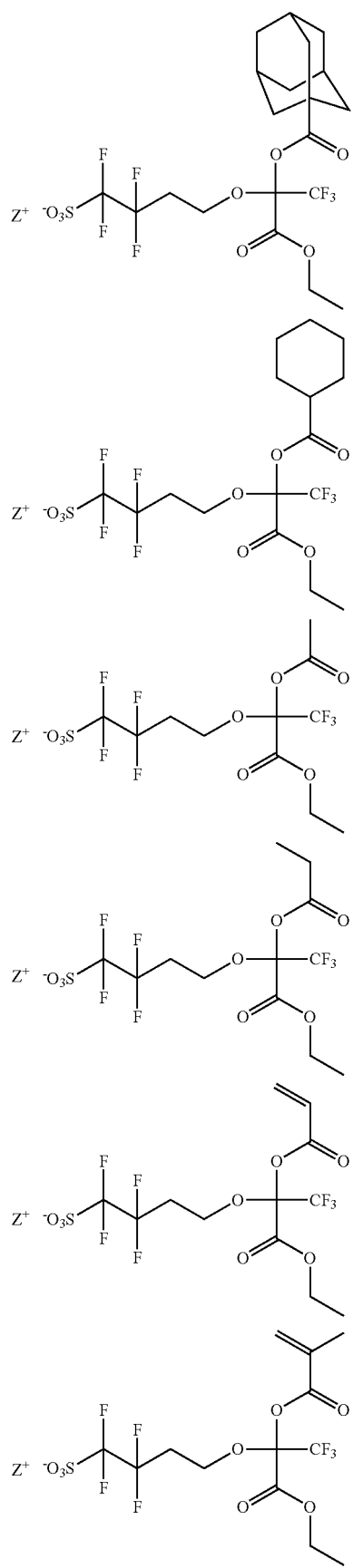
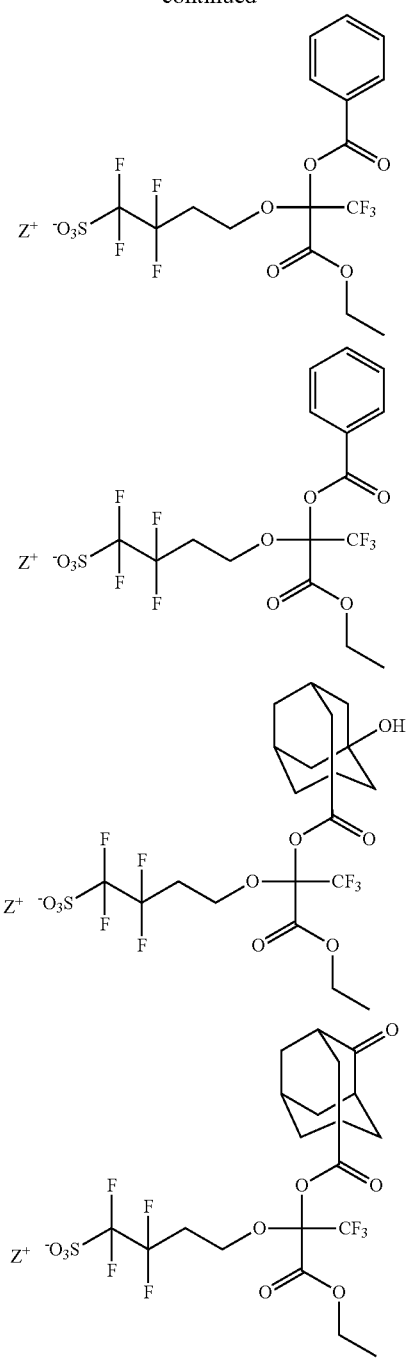

In each formula, $Z^+$ is as defined above.

Examples of the organic cation represented by $Z^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, and an arylsulfonium cation is more preferable. Herein, the arylsulfonium includes those having one, two or three aryl groups.

Preferable examples of the organic cation represented by $Z^+$ include the organic cations represented by the formulae (b2-1) to (b2-4):

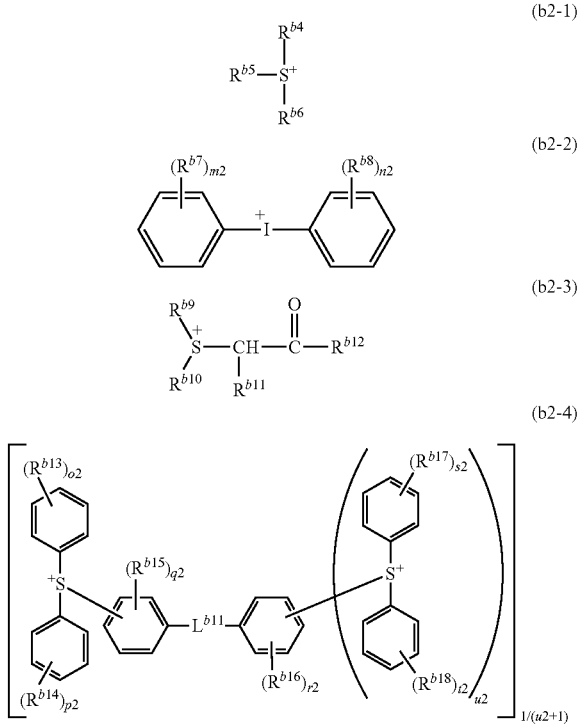

(b2-1)
(b2-2)
(b2-3)
(b2-4)

wherein $R^{b4}$, $R^{b5}$ and $R^{b6}$ independently represent a C1-C30 alkyl group in which a hydrogen atom can be replaced by a hydroxy group, or a C1-C18 alkoxy group, a C6-C36 aromatic hydrocarbon group, a C3-C12 alicyclic hydrocarbon group in which a hydrogen atom can be replaced by a halogen atom, a C2-C4 acyl group or a glycidyloxy group, and a C6-C18 aromatic hydrocarbon group in which a hydrogen atom can be replaced by a halogen atom, a hydroxy group, or C1-C12 alkoxy group, and $R^{b4}$ and $R^{b5}$, $R^{b4}$ and $R^{b6}$, or $R^{b5}$ and $R^{b6}$ can be bonded each other to form a ring containing $S^+$, $R^{b7}$ and $R^{b8}$ are independently in each occurrence a hydroxy group, a C1-C12 alkyl group or a C1-C12 alkoxy group, m2 and n2 independently represents an integer of 0 to 5, $R^{b9}$ and $R^{b10}$ independently represent a C1-C18 alkyl group or a C3-C18 alicyclic hydrocarbon group, or $R^{b9}$ and $R^{b10}$ are bonded each other to form a C1-C10 divalent acyclic hydrocarbon group which forms a 3- to 12-membered ring, preferably 3- to 7-membered ring together with the adjacent —$S^+$—, and one or more —$CH_2$— in the divalent acyclic hydrocarbon group may be replaced by an oxygen atom, sulfur atom or carbonyl group, and $R^{b11}$ represents a hydrogen atom, a C1-C18 alkyl group, or a C3-C18 alicyclic hydrocarbon group, or a C6-C18 aromatic hydrocarbon group, and $R^{b12}$ represents a C1-C12 alkyl group where a hydrogen atom can be replaced by a C6-C18 aromatic hydrocarbon group; a C3-C18 alicyclic hydrocarbon group; and a C6-C18 aromatic hydrocarbon group optionally substituted with C1-C12 alkoxy group or C1-C12 alkylcarbonyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by an oxygen atom, sulfur atom or carbonyl group, and $R^{b13}$, $R^{b14}$, $R^{b15}$, $R^{b16}$, $R^{b17}$ and $R^{b18}$ independently represent a hydroxy group, a C1-C12 alkyl group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

Examples of the alkyl group represented by each substituent include a methyl group, an ethyl group, a propyl group, an isopropyl group, a butyl group, a sec-butyl group, a tert-butyl group, a pentyl group, a hexyl group, an octyl group, and a 2-ethylhexyl group. The alkyl group represented by $R^{b9}$ to $R^{b12}$ has preferably 1 to 12 carbon atoms.

Examples of the alkyl group where a hydrogen atom has been replaced by an alicyclic hydrocarbon group include 1-(adamantane-1-yl)alkane-1-yl group.

The alicyclic hydrocarbon group represented by each substituent may be monocyclic or polycyclic, a hydrogen atom of which can be replaced by an alkyl group. When a hydrogen atom of it has been replaced by an alkyl group, the total number of carbon atoms is 20 or less.

Examples of the monocyclic alicyclic hydrocarbon group include a cycloalkyl group such as a cyclopropyl group, a cyclobutyl group, a cyclopentyl group, a cyclohexyl group, a cycloheptyl group, a cyclodecyl group.

Examples of the polycyclic alicyclic hydrocarbon group include a decahydronaphtyl group, an adamantyl group, a nobornyl group, and the following ones.

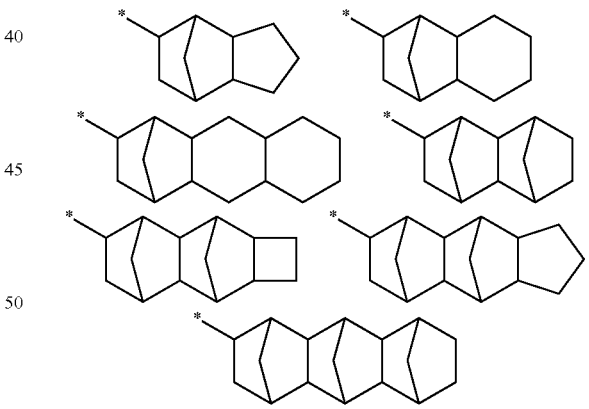

The alicyclic hydrocarbon group represented by $R^{b9}$ to $R^{b12}$ has preferably 4 to 12 carbon atoms.

Examples of the alicyclic hydrocarbon group where a hydrogen atom has been replaced by an alkyl group include a methylcyclohexyl group, a 2-alkyladamantane-2-yl group, a methylnorbornyl group, and an isobornyl group.

Preferable examples of the aromatic hydrocarbon group represented by each substituent include substituted or unsubstituted phenyl group such as a phenyl group, a tolyl group, a xylyl group, a cumenyl group, a mesityl group, a 4-ethylphenyl group, 4-tert-butylphenyl group, 4-cyclohexylphenyl group, a 4-adamantylphenyl group, a 2,6-diethylphenyl group, a 2-methyl-6-ethylphenyl group; a biphenyl group, a naphtyl group, a phenanthryl group.

Preferable examples of the aromatic hydrocarbon group where a hydrogen atom has been replaced by an alkoxy group include 4-methoxyphenyl group.

Preferable examples of the alkyl group where a hydrogen atom has been replaced by an aromatic hydrocarbon group, i.e., an aralkyl group, include a benzyl group, a phenethyl group, a phenylpropyl group, a trityl group, a naphthylmethyl group and a naphthylethyl group.

When the aromatic hydrocarbon group has an alkyl group or an alicyclic hydrocarbon group as a substituent, the substituent is preferably a C1-C12 alkyl group or a C3-C18 alicyclic hydrocarbon group.

Examples of the alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of the C2-C4 acyl group include an acetyl group, a propyonyl group and a butyryl group.

Examples of the halogen atom include a fluorine atom, a chlorine atom, a bromine atom and an iodine atom.

Preferable examples of the alkylcarbonyloxy group include a methylcarbonyloxy group, an ethylcarbonyloxy group, n-propylcarbonyloxy group, an isopropylcarbonyloxy group, n-butylcarbonyloxy group, sec-butylcarbonyloxy group, a tert-butylcarbonyloxy group, a pentylcarbonyloxy group, a hexylcarbonyloxy group, an octylcarbonyloxy group and 2-ethyl hexylcarbonyloxy group.

The ring containing $S^+$ formed by bonding $R^{b4}$ and $R^{b5}$, $R^{b4}$ and $R^{b6}$, or $R^{b5}$ and $R^{b6}$ each other may be a monocyclic ring, a polycyclic ring, an aromatic ring, a non-aromatic ring, a saturated ring or a unsaturated ring. The ring can contain one or more sulfur atom or oxygen atom in addition to $S^+$. The ring preferably has 3 to 18 carbon atoms, and more preferably has 4 to 13 carbon atoms.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include oxocyclopentane ring, oxocyclohexane ring, oxonorbornane ring and oxoamadantane ring. A C1-C5 divalent acyclic hydrocarbon group is preferable.

Among the above-mentioned cations, preferred is the cation represented by the formula (b2-1), more preferred is the cation represented by the formula (b2-1) in which any of $R^{b4}$, $R^{b5}$ and $R^{b6}$ is an aromatic hydrocarbon group, still more preferred is the cation represented by the formula (b2-1-1), especially more preferred is a triphenylphosphonium cation, a diphenyltolylsulfonium cation or a tritolylsulfonium cation.

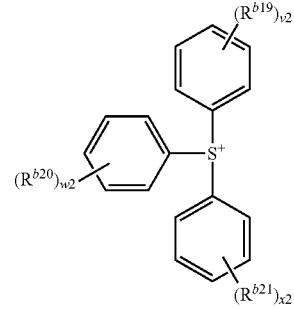

(b2-1-1)

wherein $R^{b19}$, $R^{b20}$ and $R^{b21}$ are independently in each occurrence a halogen atom (preferably a fluorine atom), a hydroxy group, a C1-C12 alkyl group, a C1-C12 alkoxy group, or a C3-C18 alicyclic hydrocarbon group; or $R^{b19}$ and $R^{b20}$, $R^{b19}$ and $R^{b21}$ or $R^{b20}$ and $R^{b21}$ can be bonded each other to form a ring together with $S^+$; and v2, w2 and x2 each independently represent an integer of 0 to 5.

Each of $R^{b19}$, $R^{b20}$ and $R^{b21}$ is preferably a halogen atom (preferably a fluorine atom), a hydroxy group, a C1-C12 alkyl group and a C1-C12 alkoxy group, and more preferably a halogen atom (preferably a fluorine atom) and a C1-C6 alkyl group.

The v2, w2 and x2 each independently represent 0 or 1.

The cation represented by the formula (b2-1-1) includes specifically those mentioned in JP2010-204646A1.

The salt represented by the formula (II) consists of any one of the above-mentioned anions and any one of the above-mentioned cations, specifically those represented by following ones.

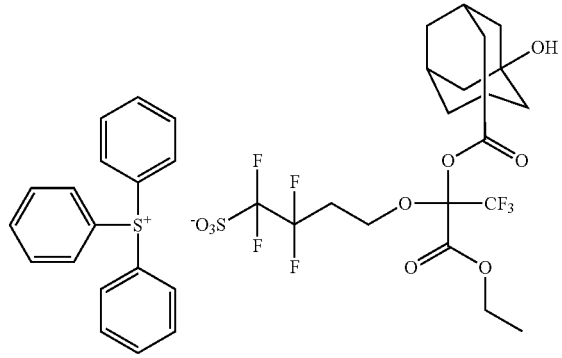

(II-1)

(II-2)
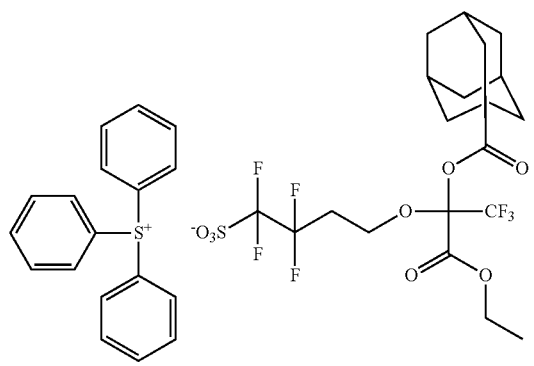
(II-3)
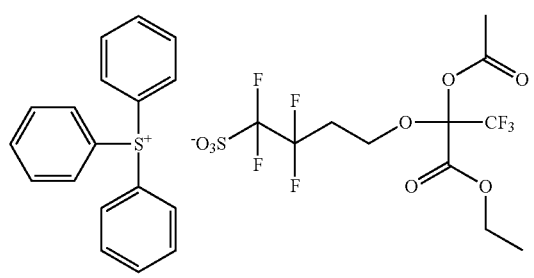
(II-4)
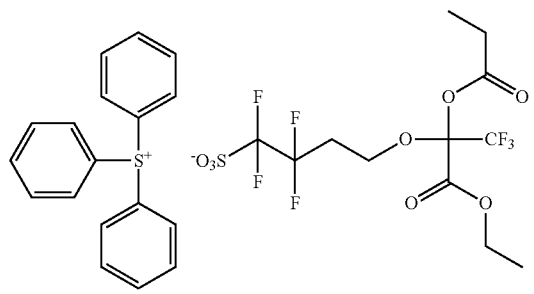
(II-5)
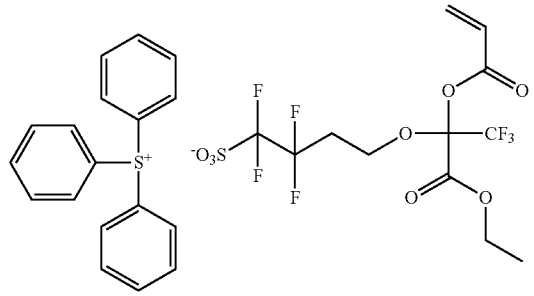
(II-6)
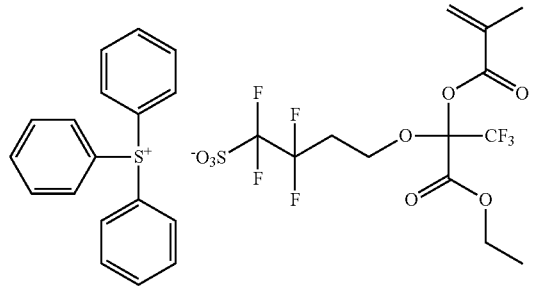
(II-7)
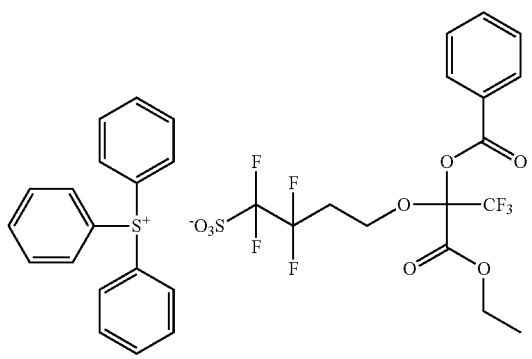
(II-8)
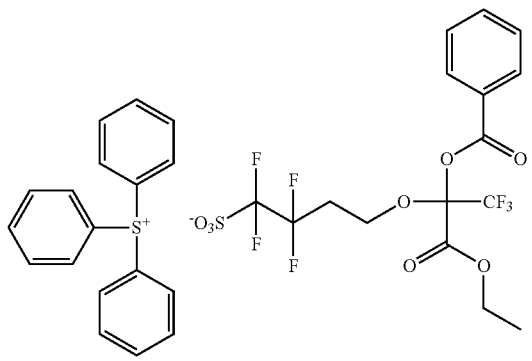
(II-9)
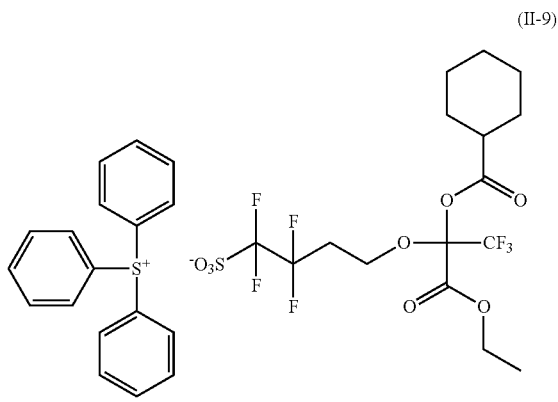
(II-10)
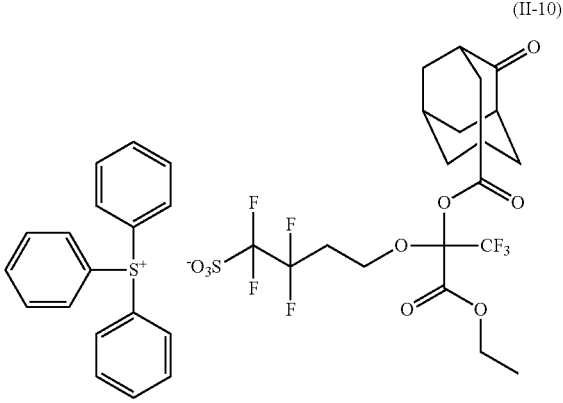

(II-11)
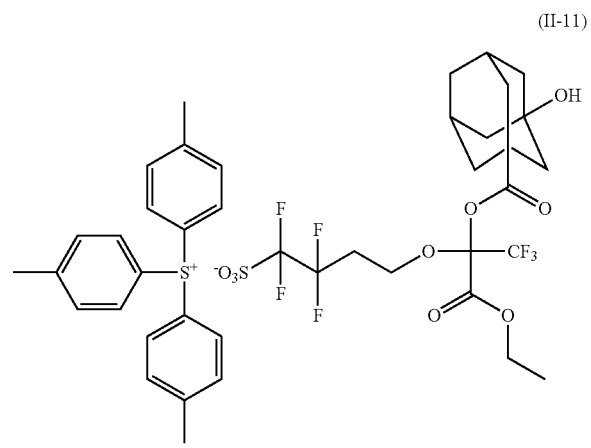
(II-15)
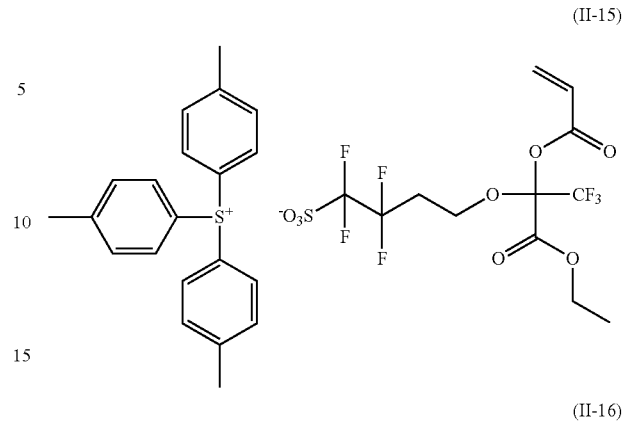
(II-12)
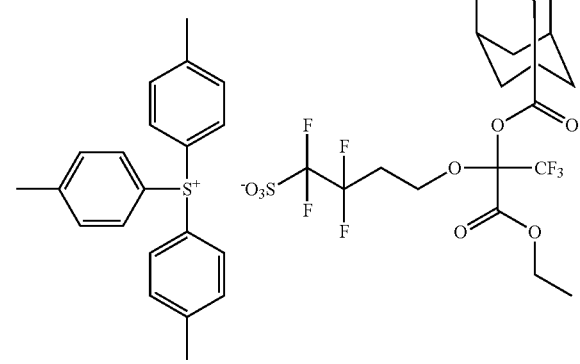
(II-16)
(II-13)
(II-17)
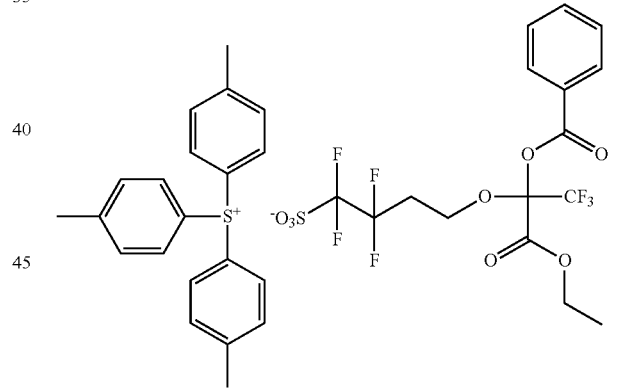
(II-14)
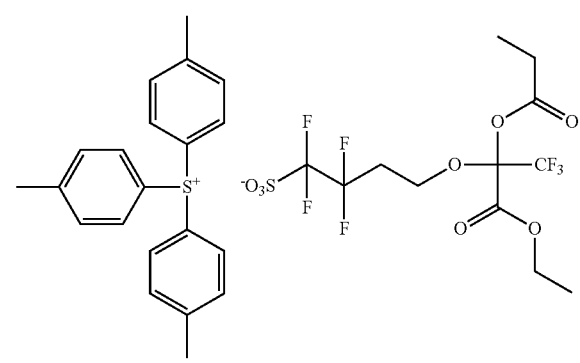
(II-18)
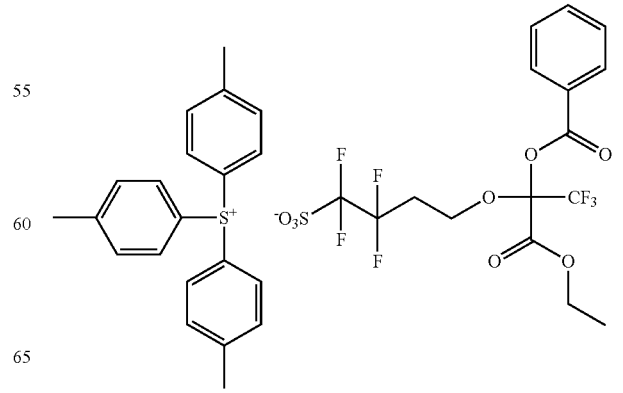

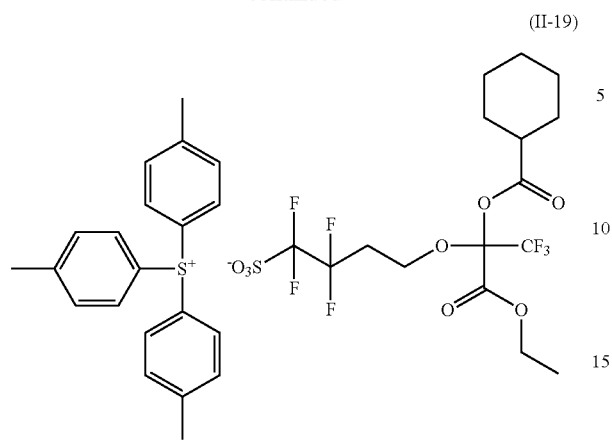
(II-19)
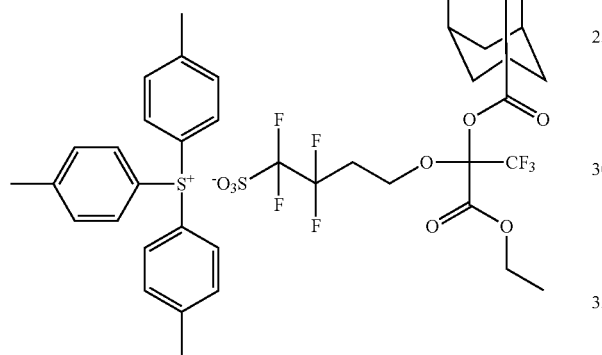
(II-20)
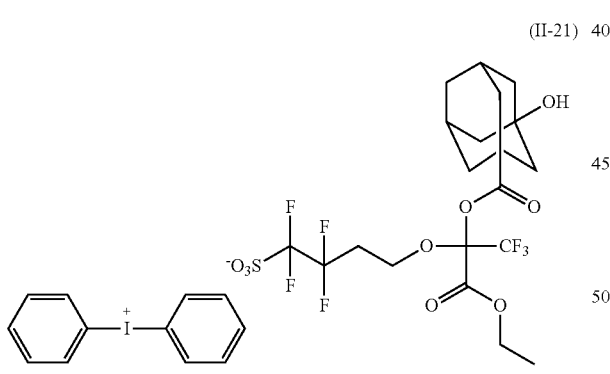
(II-21)
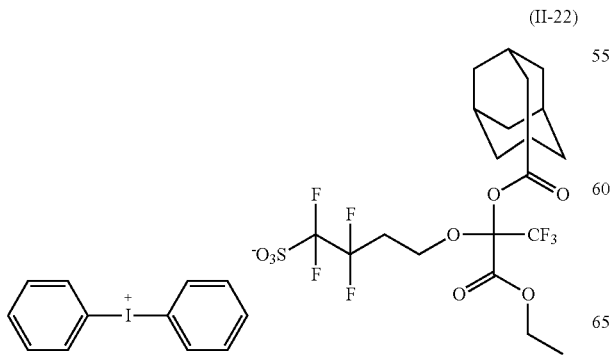
(II-22)
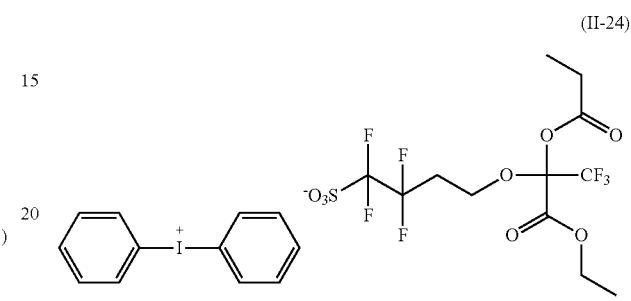
(II-23)
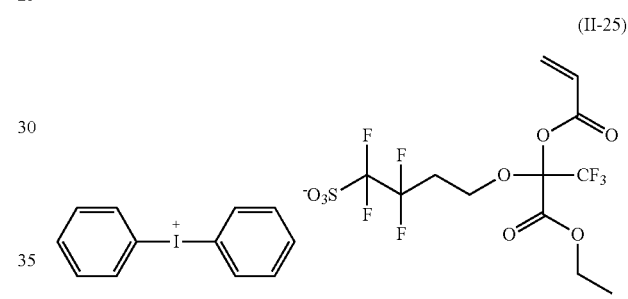
(II-24)
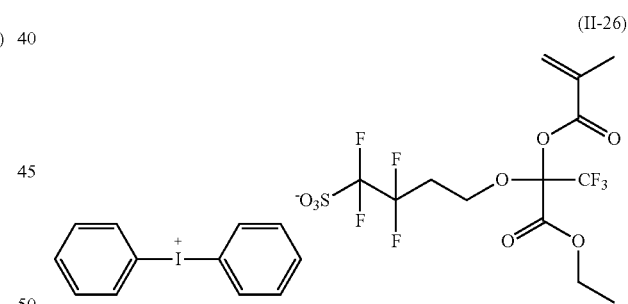
(II-25)
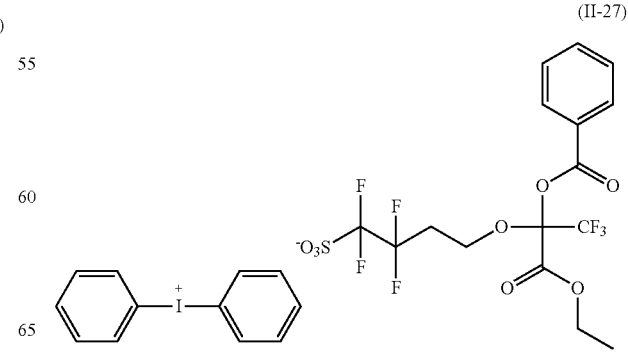
(II-26)
(II-27)

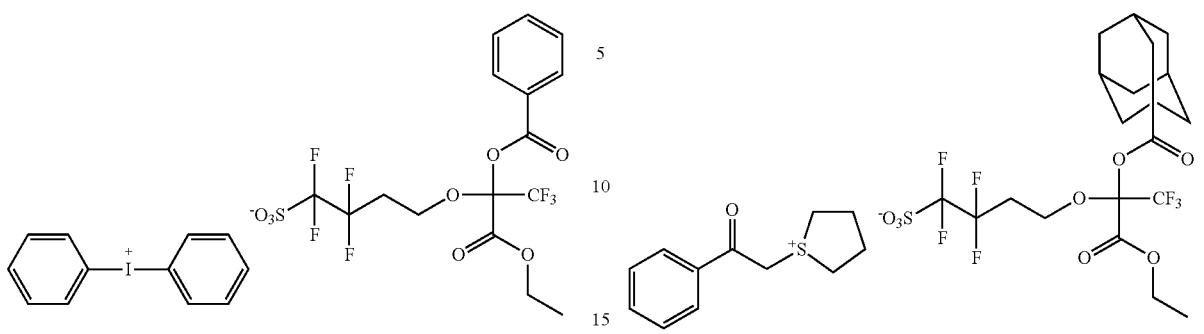
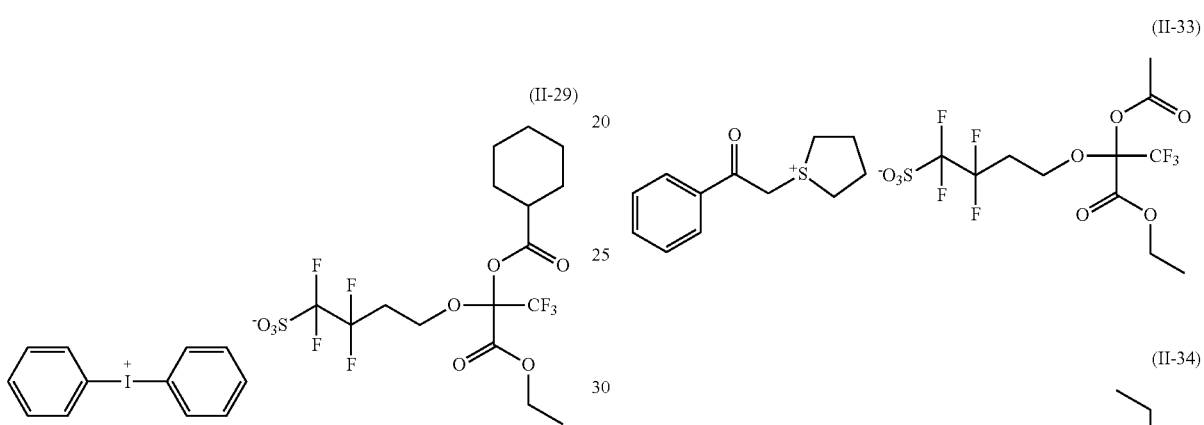
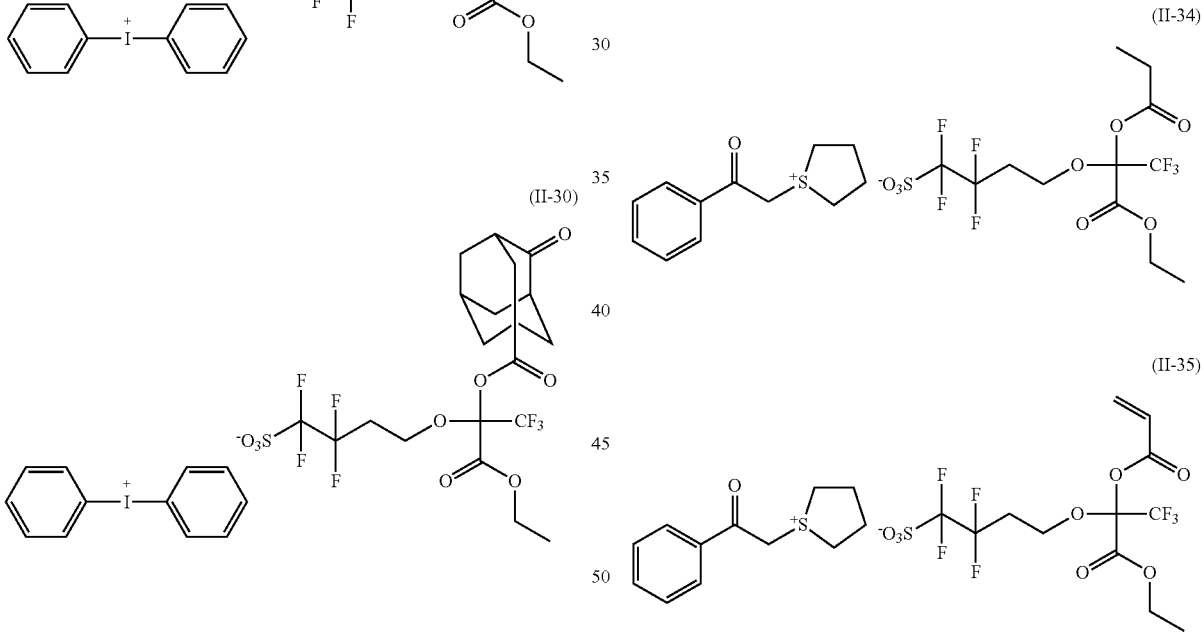
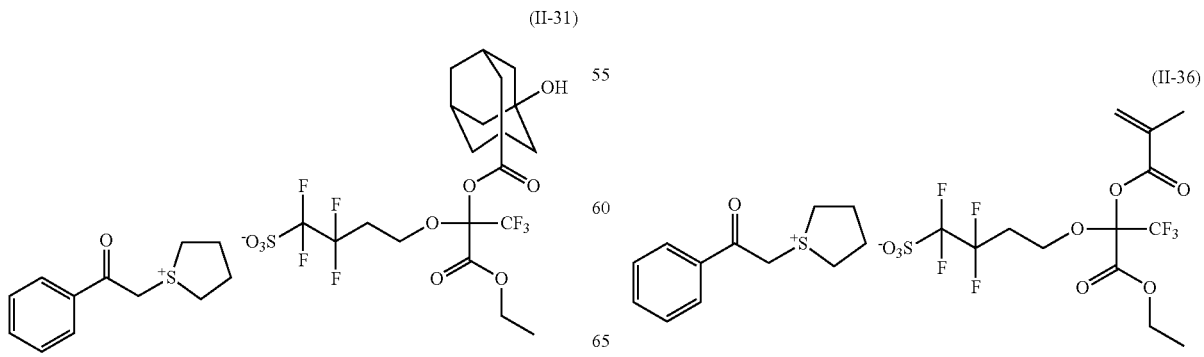

(II-37)

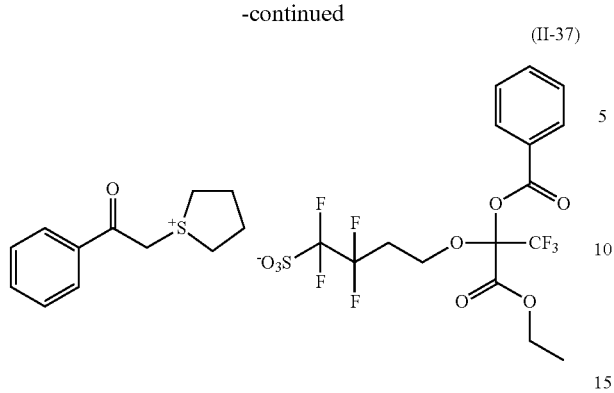

(II-38)

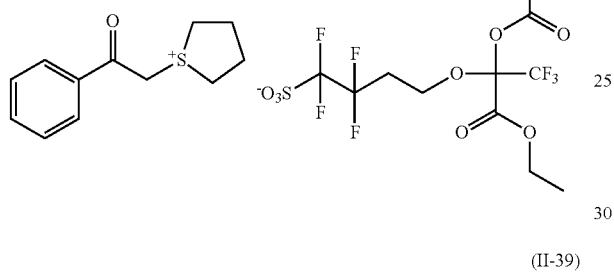

(II-39)

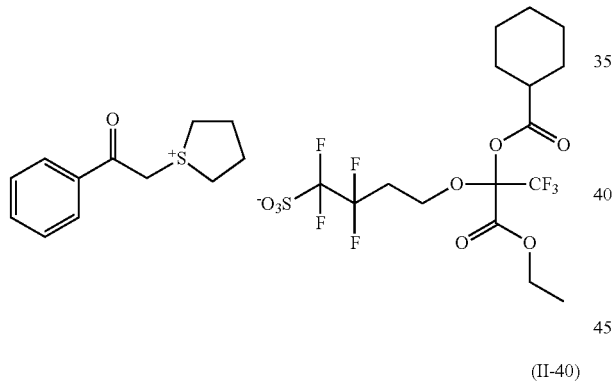

(II-40)

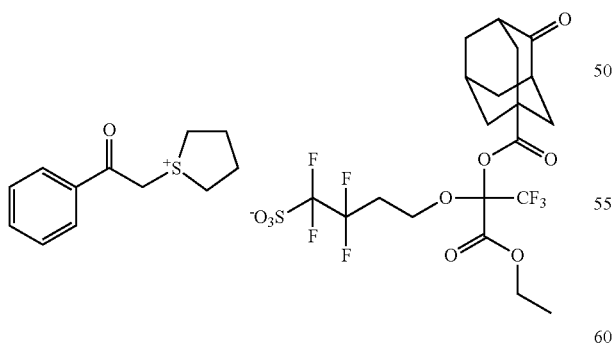

The salt represented by formula (II) is available on the market.

The salt represented by formula (II) can be obtained by reacting a salt represented by formula (II-0-1) with a compound represented by formula (II-0-2) in a solvent such as chloroform:

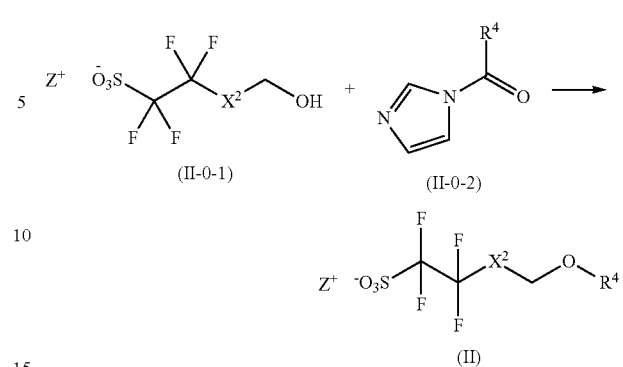

where $X^2$, $R^4$ and $Z^+$ are as defined above.

The salt represented by formula (II-0-1) includes the following salts which can be obtained by a method described in US2007/298352A1

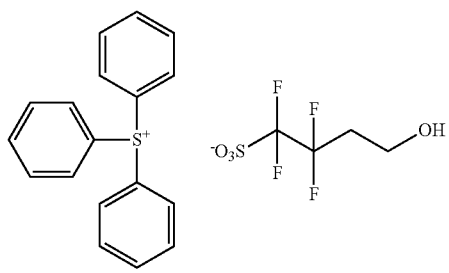

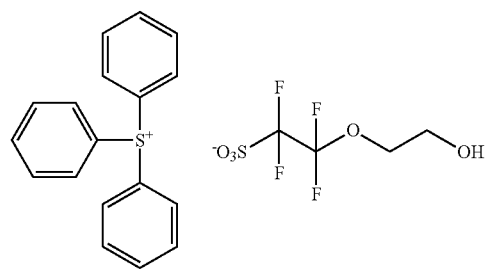

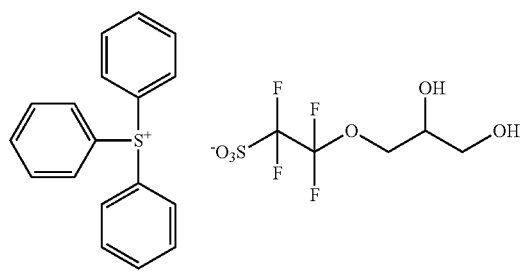

The compound represented by formula (II-0-2) can be obtained by reacting a salt represented by formula (II-0-3) with a compound represented by formula (II-0-4) in a solvent such as chloroform:

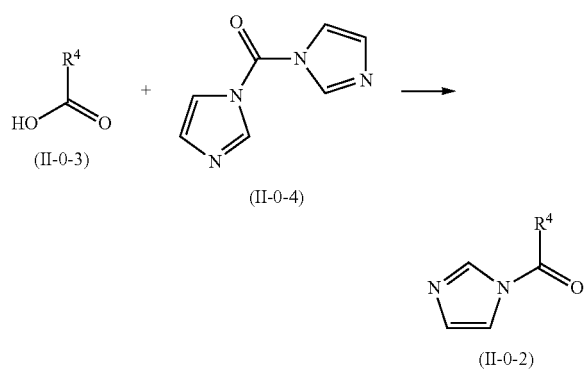

where R⁴ is as defined above.
The compound represented by formula (II-0-3) includes the following compounds which are available on the market.

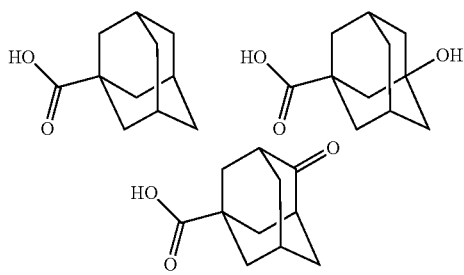

The salt represented by formula (IIA) can be obtained by reacting a salt represented by formula (IIA-1) with a compound represented by formula (IIA-2) in a solvent such as chloroform:

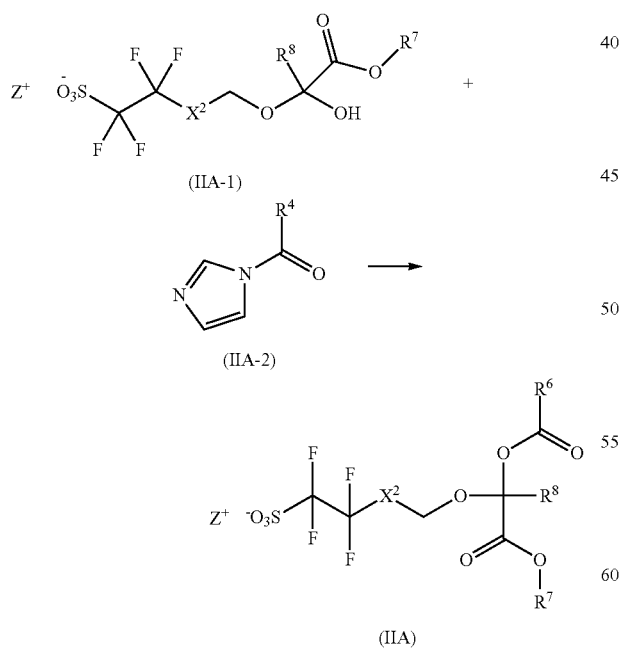

where $X^2$, $R^6$, $R^7$, $R^8$ and $Z^+$ are as defined above.
The salt represented by formula (IIA-1) can be obtained by reacting a salt represented by formula (II-0-1) with a compound represented by formula (IIA-4), in the presence of an acid catalyst such as p-toluenesulfonic acid, in a solvent such as dimethylformamide.

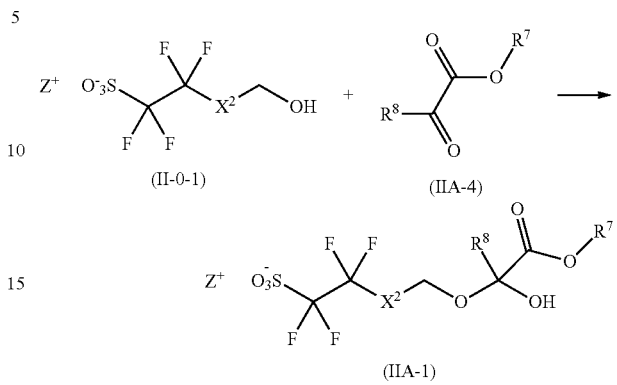

where $X^2$, $R^7$, $R^8$ and $Z^+$ are as defined above.
The salt represented by formula (IIA-4) includes trifluoropyruvic acid ester.
The salt represented by formula (IIA-2) can be obtained by reacting a salt represented by formula (IIA-5) with a compound represented by formula (IIA-6) in a solvent such as chloroform;

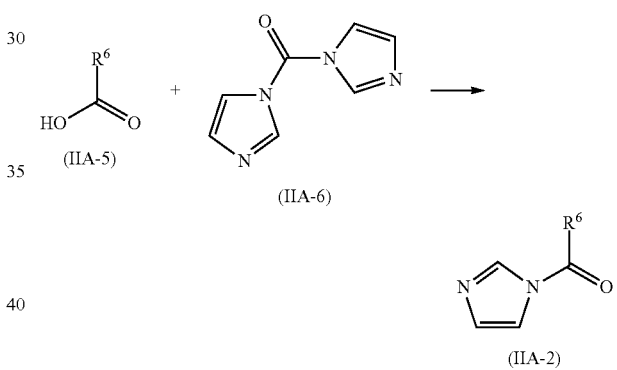

where $R^6$ is as defined above.
The salt represented by formula (IIA-5) includes the following compounds.

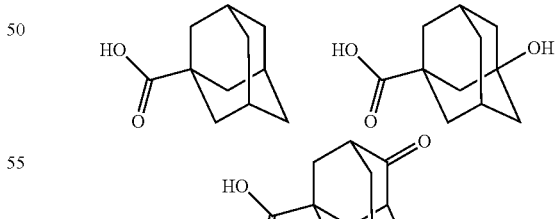

The photoresist composition comprises the salt represented by formula (II) singly or in combination of two or more of them.
The photoresist composition may comprise an acid generator other than the salt represented by formula (II). Such acid generator other than the salt is sometimes referred to as "acid generator (B)".

The acid generator is a compound which can be decomposed by light or radiation to generate an acid. The acid generators may be either ionic or non-ionic one. The acid generator can be used singly or in combination of two or more of them.

The non-ionic acid generator includes organic halide, sulfonate esters (e.g., 2-nitrobenzylester, aromatic sulfonate, oxime sulfonate, N-sulfonyloxyimide, N-sulfonyloxyimide, sulfonyl oxyketone, diazonaphthoquinone 4-sulfonate) and sulfone (e.g., disulfone, ketosulfone, sulfonyldiazomethane). The ionic acid generator includes an onium salt comprising an onium cation (e.g., a diazonium salt, a phosphonium salt, a sulfonium salt, an iodonium salt). Anions of the onium salts include a sulfonic acid anion, a sulfonylimide anion and a sulfonylmethide anion.

The acid generator includes compounds which generate an acid upon radiation, which are described in JP63-26653A1, JP55-164824A1, JP62-69263A1, JP63-146038A1, JP63-163452A1, JP 62-153853A1, JP63-146029A1, U.S. Pat. No. 3,779,778, U.S. Pat. No. 3,849,137, German patent No. 3914407 and European patent No. 126712.

The acid generator (B) is preferably a fluorine-containing acid generator, more preferably a salt represented by formula (B1):

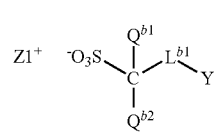

(B1)

wherein $Q^{b1}$ and $Q^{b2}$ each independently represent a fluorine atom or a C1-C6 perfluoroalkyl group,
$L^{b1}$ represents a single bond or a C1-C17 divalent saturated hydrocarbon group where a methylene group can be replaced by an oxygen atom or a carbonyl group,
Y represents a hydrogen atom or a C3-C18 alicyclic hydrocarbon group where a methylene group can be replaced by an oxygen atom, a sulfonyl group or a carbonyl group and where a hydrogen atom can be replaced by a substituent, and
$Z1^+$ represents an organic cation.

Examples of the perfluoroalkyl group represented by $Q^{b1}$ and $Q^{b2}$ include a trifluoromethyl group, a pentafluoroethyl group, a heptafluoropropyl group, a nonafluorobutyl group, an undecafluoropentyl group and a tridecafluorohexyl group. It is preferred that $Q^{b1}$ and $Q^{b2}$ each independently represent a fluorine atom or a trifluoromethyl group, and it is more preferred that $Q^{b1}$ and $Q^{b2}$ are fluorine atoms.
Examples of the divalent saturated hydrocarbon group represented by $L^{b1}$ include linear alkanediyl groups, branched chain alkanediyl groups,
a monocyclic divalent alicyclic hydrocarbon groups, a polycyclic divalent alicyclic hydrocarbon groups and combinations of them. Specific examples of them include
linear alkanediyl groups such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, an ethane-1,1-diyl group, a propane-1,1-diyl group;
branched chain alkanediyl groups including a group formed by attaching a side chain to a linear alkanediyl group, such as a butan-1,3-diyl group, a2-methylpropane-1,3-diyl group, a 2-methylpropane-1,2-diyl group, a pentane-1,4-diyl group, and a 2-methylbutane-1,4-diyl group;
a monocyclic divalent alicyclic hydrocarbon groups such as a cyclobutan-1,3-diyl group, cyclopentane-1,3-diyl group, a cyclohexane-1,2-diyl group, a 1-methylcyclohexane-1,2-diyl group, cyclohexane-1,4-diyl group, cyclooctane-1,2-diyl group, and a cyclooctane-1,5-diyl group; and
polycyclic divalent alicyclic hydrocarbon groups such as a norbornane-2,3-diyl group, norbornane-1,4-diyl group, a norbornane-2,5-diyl group, an amadantane-1,2-diyl group, an amadantane-1,5-diyl group and an amadantane-1,6-diyl group.

When $L^{b1}$ represents a divalent saturated hydrocarbon group in which a methylene group has been replaced by an oxygen atom or a carbonyl group, examples of $L^{b1}$ include the moiety represented by any one of formulae (b1-1) to (b1-7) as follow;

(b1-1)

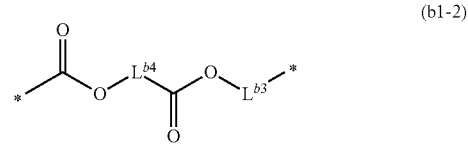

(b1-2)

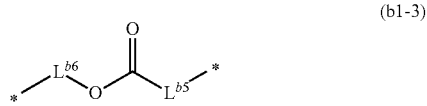

(b1-3)

(b1-4)

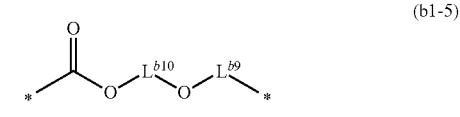

(b1-5)

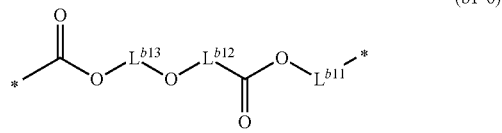

(b1-6)

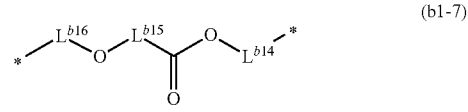

(b1-7)

wherein $L^{b2}$ represents a single bond or a C1-C15 divalent saturated hydrocarbon group,
$L^{b3}$ represents a single bond or a C1-C12 divalent saturated hydrocarbon group,
$L^{b4}$ represents a C1-C13 divalent saturated hydrocarbon group provided that the total carbon atoms of $L^{b3}$ and $L^{b4}$ is up to 13,
$L^{b5}$ represents a single bond or a C1-C14 divalent saturated hydrocarbon group,
$L^{b6}$ represents a C1-C15 divalent saturated hydrocarbon group provided that the total carbon atoms of $L^{b5}$ and $L^{b6}$ is up to 15,
$L^{b7}$ represents a single bond or a C1-C15 divalent saturated hydrocarbon group,
$L^{b8}$ represents a C1-C15 divalent saturated hydrocarbon group with the proviso that total carbon number of $L^{b7}$ and $L^{b8}$ is up to 16, $L^{b9}$ represents a single bond or a C1-C13 divalent saturated hydrocarbon group,
$L^{b10}$ represents a C1-C14 divalent saturated hydrocarbon group, with the proviso that total carbon number of $L^{b9}$ and $L^{b10}$ is up to 14,
$L^{b11}$ and $L^{b12}$ each independently represent a single bond or a C1-C11 divalent saturated hydrocarbon group, and
$L^{b13}$ represents C1-C12 divalent saturated hydrocarbon group, with the proviso that total carbon number of $L^{b11}$, $L^{b12}$ and $L^{b13}$ is up to 12,
$L^{b14}$ and $L^{b15}$ each independently represent a single bond or a C1-C13 divalent saturated hydrocarbon group, and
$L^{b16}$ represents C1-C14 divalent saturated hydrocarbon group, with the proviso that total carbon number of $L^{b14}$, $L^{b15}$ and $L^{b16}$ is up to 14,
* represents a binding position, * of the left side represents a binding position to $-C(Q^1)(Q^2)-$, and * of the right side represents a binding position to $-(C=O)-$.

Examples of the moiety represented by formula (b1-1) include one represented as follows.

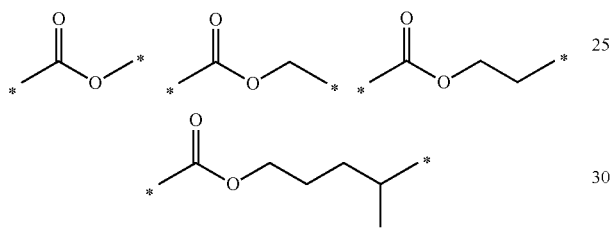

Examples of the moiety represented by formula (b1-2) include one represented as follows.

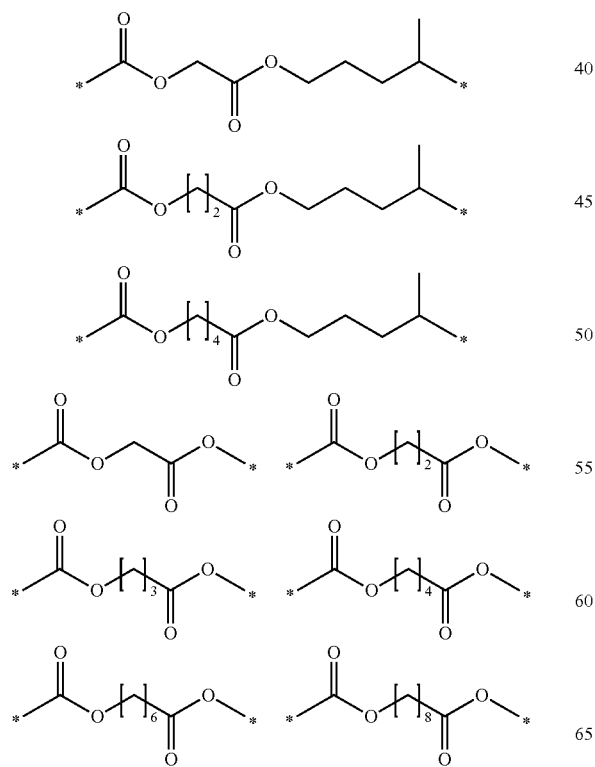

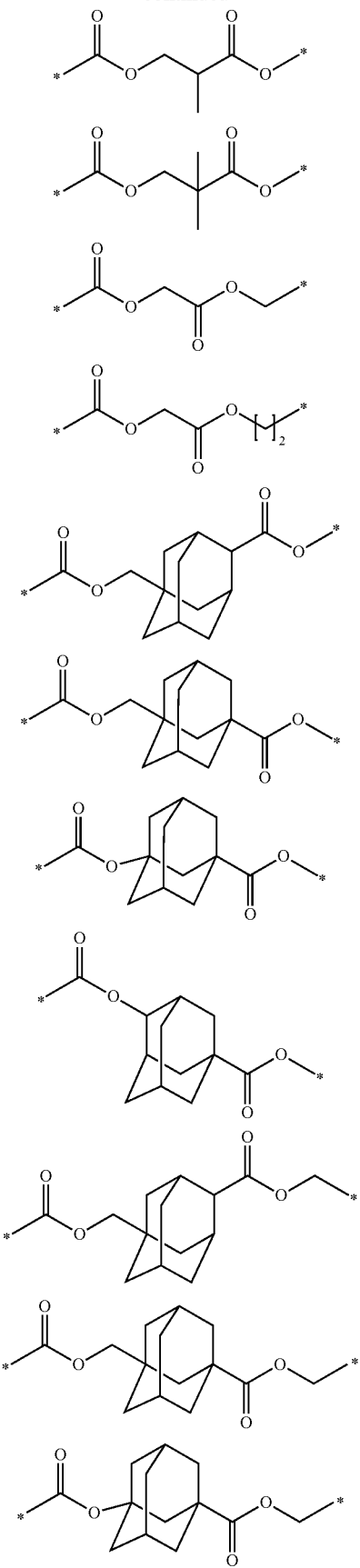

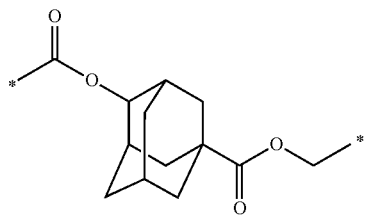
Examples of the moiety represented by formula (b1-3) include one represented as follows.
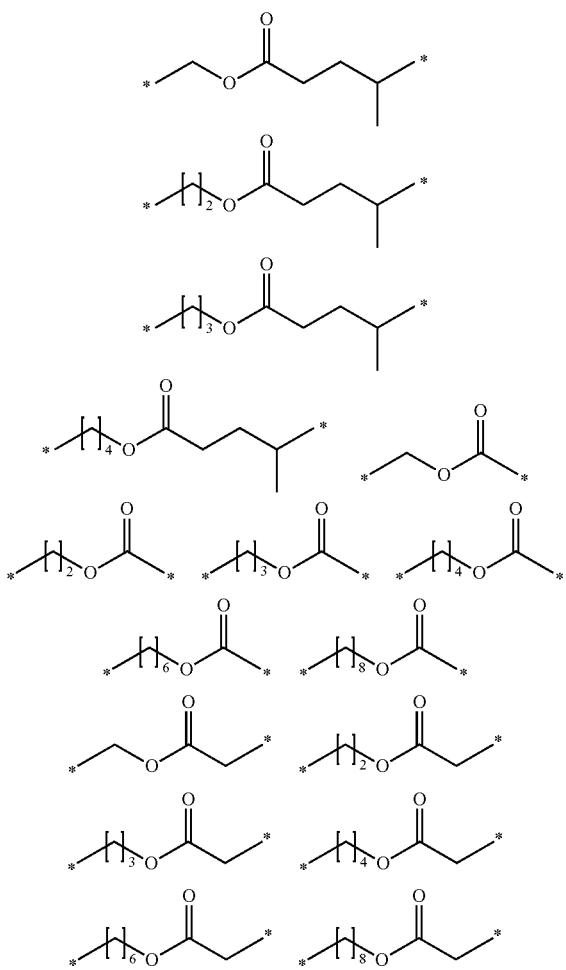
Examples of the moiety represented by formula (b1-4) include one represented as follows.
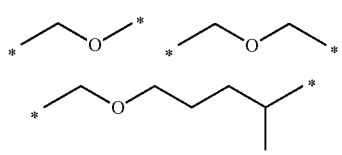
Examples of the moiety represented by formula (b1-5) include one represented as follows.
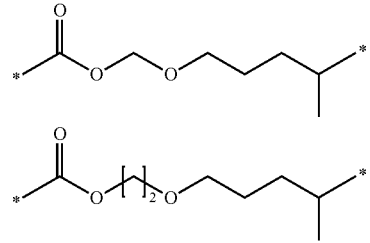
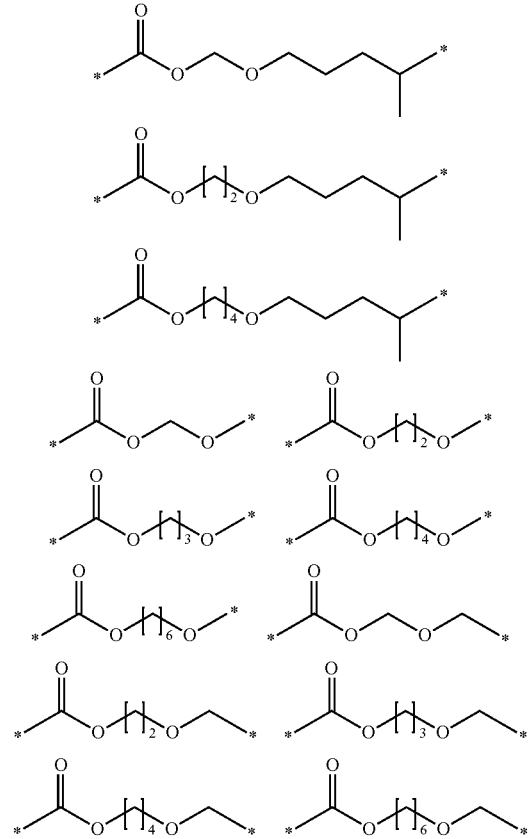
Examples of the moiety represented by formula (b1-6) include one represented as follows.
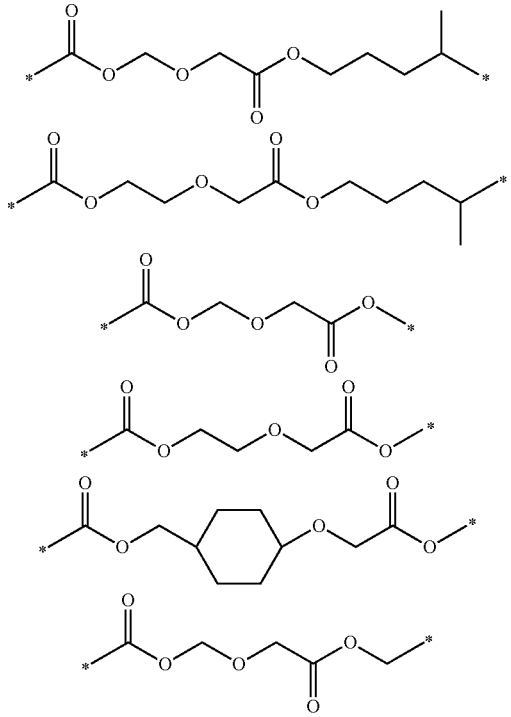

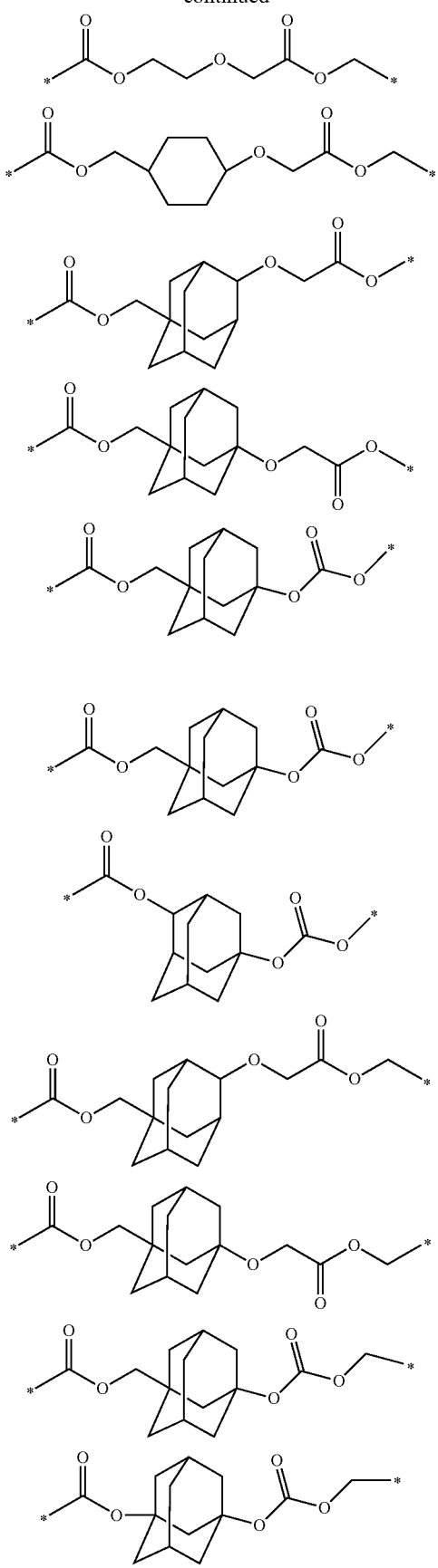

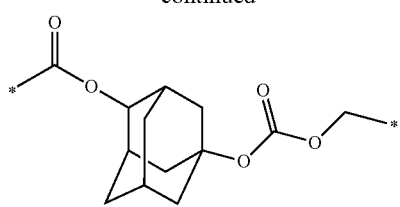

Examples of the moiety represented by formula (b1-7) include one represented as follows.

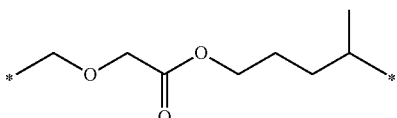
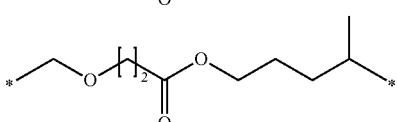
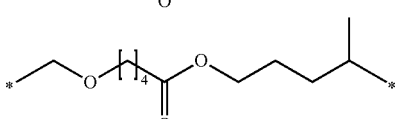
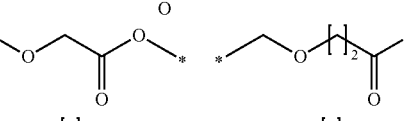
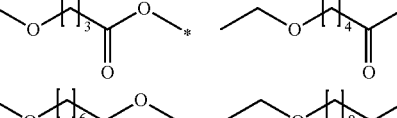
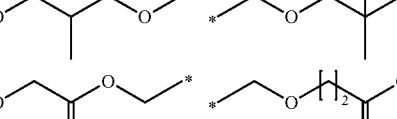
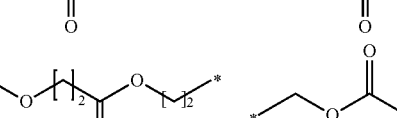
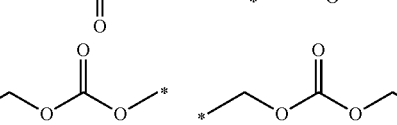

$L^{b1}$ is preferably the moieties represented by any one of formulae (b1-1) to (b1-4), more preferably the moieties represented by any formula (b1-1) or (b1-2), still more preferably the moieties represented by formula (b1-1). Among the moieties represented by formula (b1-1), preferred are those in which $L^{b2}$ represents a single bond or a methylene group, and more preferred are one in which $L^{b2}$ represents a single bond, i.e., *—CO—O— where represents a binding position to —C($Q^1$)($Q^2$)-.

Examples of the alicyclic hydrocarbon group represented by Y include those represented by formulae (Y1) to (Y11).

Examples of the alicyclic hydrocarbon group represented by Y, in which a methylene group can be replaced by an oxygen atom, a sulfonyl group or a carbonyl group, include further include those represented by formulae (Y12) to (Y26).

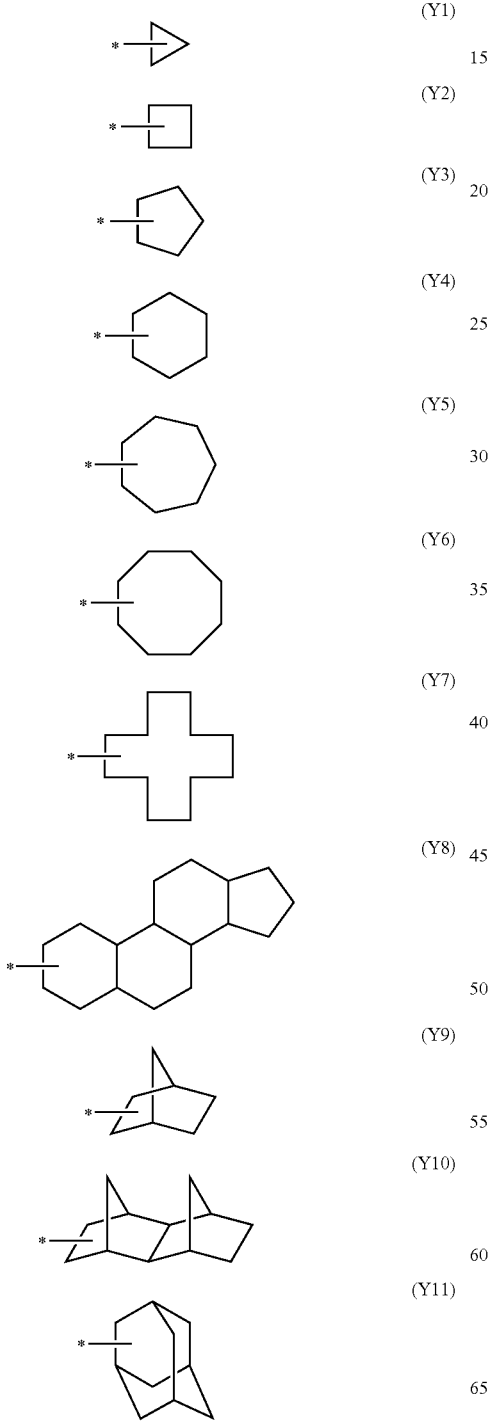

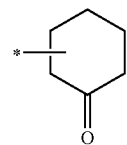 (Y12)

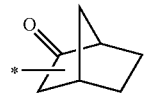 (Y13)

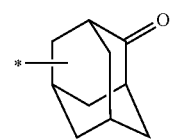 (Y14)

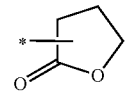 (Y15)

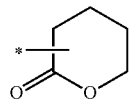 (Y16)

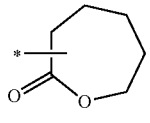 (Y17)

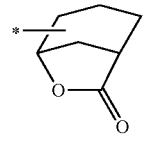 (Y18)

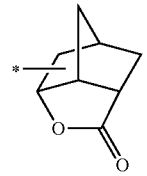 (Y19)

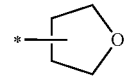 (Y20)

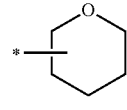 (Y21)

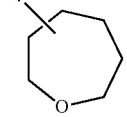 (Y22)

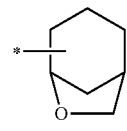 (Y23)

-continued (Y24)

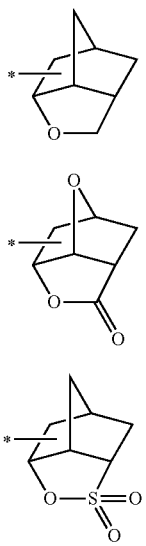

(Y25)

(Y26)

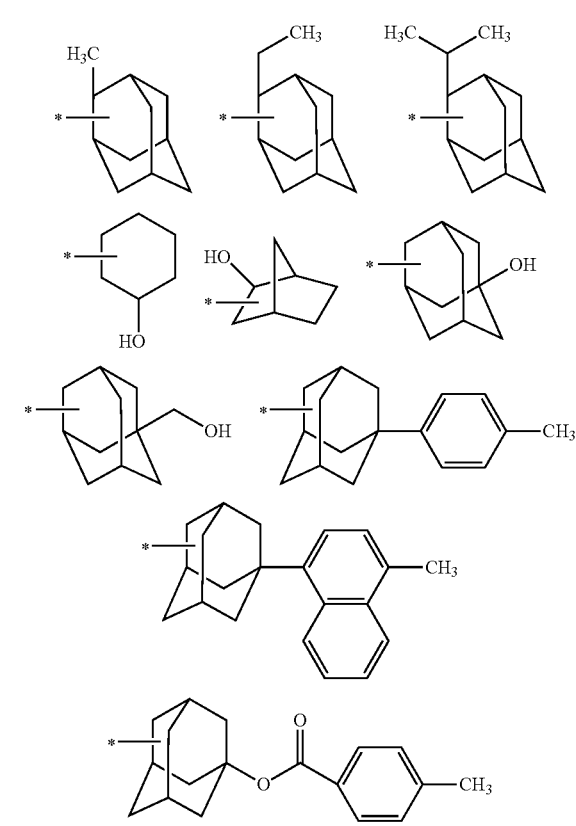

Among them, preferred are those represented by formulae (Y1) to (Y19), more preferred are those represented by formulae (Y11), (Y14), (Y15) and (Y19), and still more preferred are those represented by formulae (Y11) and (Y14).

Examples of the substituents for the alicyclic hydrocarbon group represented by Y include a halogen atom, a hydroxy group, an oxo group, a C1-C12 alkyl group, a C1-C12 hydroxy-containing alkyl group, a C3-C16 alicyclic hydrocarbon group, a C1-C12 alkoxy group, a C6-C18 aromatic hydrocarbon group optionally substituted with a C1-C4 alkyl group, a C7-C21 aralkyl group, a C2-C4 acyl group, a glycidyloxy group, or —$(CH_2)_{j2}$—O—CO—$R_{b1}$ group where $R_{b1}$ represents a C1-C16 alkyl group, a C3-C16 alicyclic hydrocarbon group, or a C6-C18 aromatic hydrocarbon group optionally substituted with a C1-C4 alkyl group. The symbol j2 represents an integer of 0 to 4.

Examples of the halogen atom include a fluorine atom, a chlorine atom, a bromine atom and an iodine atom.

Examples of the hydroxyl-containing alkyl group include a hydroxymethyl group and a hydroxyethyl group.

Examples of alkoxy group include a methoxy group, an ethoxy group, a propoxy group, a butoxy group, a pentyloxy group, a hexyloxy group, a heptyloxy group, an octyloxy group, a decyloxy group and a dodecyloxy group.

Examples of an aromatic hydrocarbon group include aryl groups such as a phenyl group, a naphthyl group, an antolyl group, a p-methylphenyl group, p-tert-butylphenyl group, p-adamantylphenyl group, a tolyl group, a xylyl group, a cumenyl group, a mesityl group, a biphenyl group, a phenanthryl group, a 2,6-diethylphenyl group, 2-methyl-6-ethylphenyl group.

Examples of an aralkyl group include a benzyl group, a phenethyl group, a phenylpropyl group, a naphthylmethyl group and a naphthylethyl group.

Examples of an acyl group include an acetyl group, a propionyl group and a butyryl group.

Examples of the group represented by Y include the following ones.

Y is preferably a C3-C18 alicyclic hydrocarbon group which can have a substituent, more preferably an adamantyl group which can have a substituent such as oxo group or a hydroxyl group, more preferably an adamantyl group, a hydroxyadamantyl group, or an oxoadamantyl group.

The sulfonic acid anion of the salt (B1) includes an anion represented by formulae (b1-1-1) to (b1-1-9):

(b1-1-1)

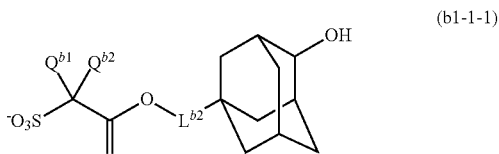

(b1-1-2)

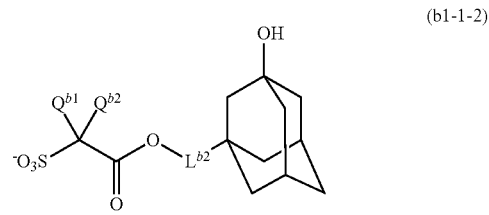

(b1-1-3)

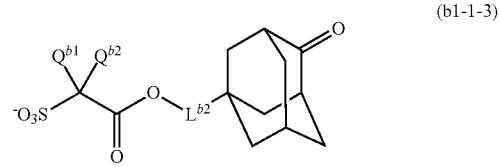

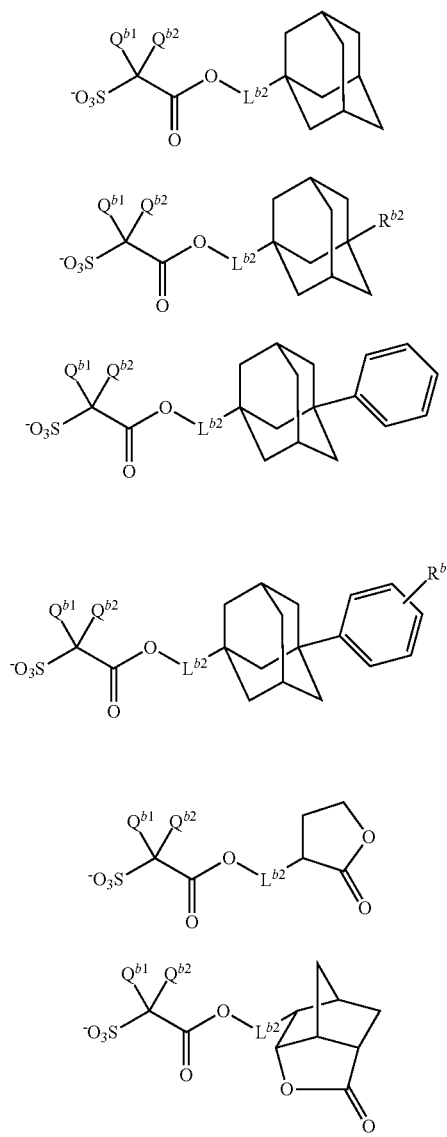
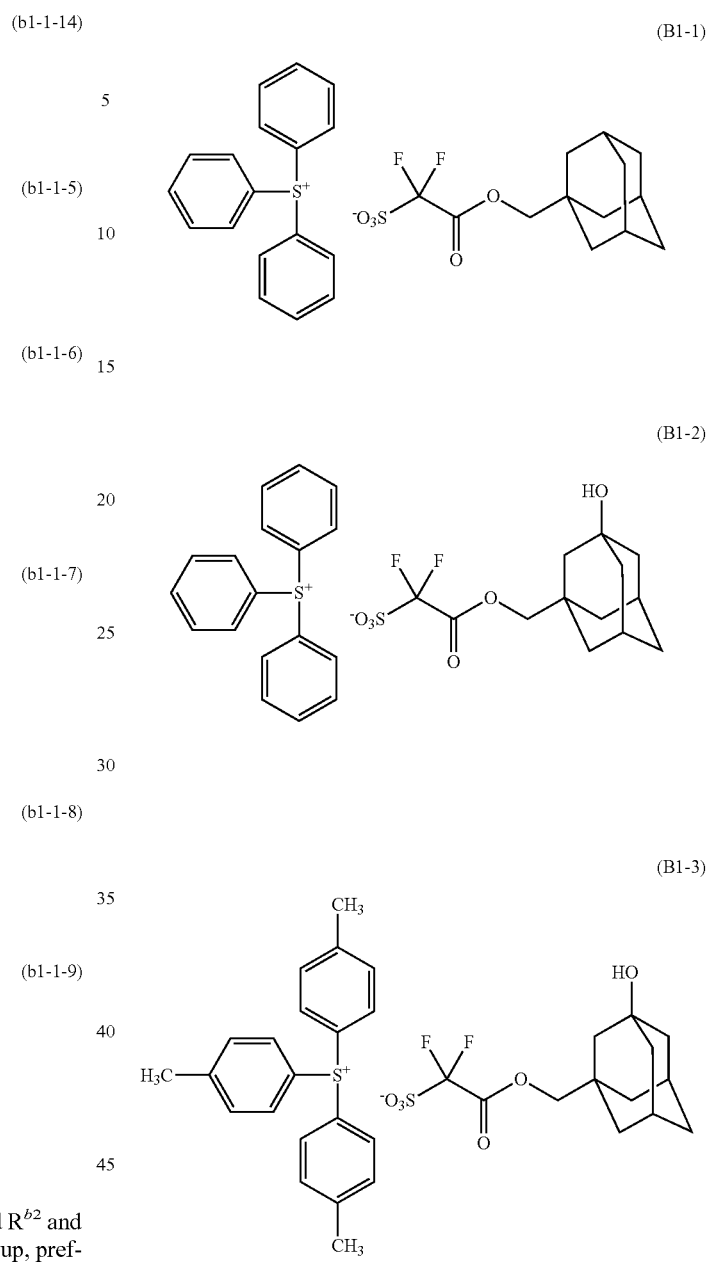

where $Q^{b1}$, $Q^{b2}$, $L^{b2}$ and Y are as defined above, and $R^{b2}$ and $R^{b3}$ each independently represent a C1-C4 alkyl group, preferably a methyl group.

Examples of sulfonic acid anions of the salt (B2) include those described in JP2010-204646A1.

Examples of the organic cation represented by $Z1^+$ include an organic onium cation such as an organic sulfonium cation, an organic iodonium cation, an organic ammonium cation, a benzothiazolium cation and an organic phosphonium cation, and an organic sulfonium cation and an organic iodonium cation are preferable, the cations represented by formulae (b2-1) to (b2-4) are more preferable, and an arylsulfonium cation is still more preferable.

Examples of the salt (B1) include the salts presented by formulae (B1-1) to (B1-20). Among them, the salts which comprise a triphenylsulfonium cation or a tritolylsulfonium cation are preferable, the salts presented by formulae (B1-1), (B1-2), (B1-3), (B1-6), (B1-7), (B1-11), (B1-12), (B1-13) and (B1-14) are more preferable.

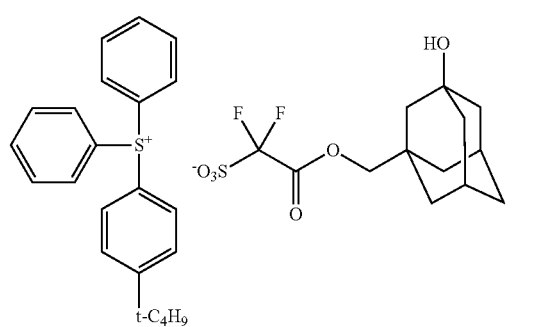

-continued
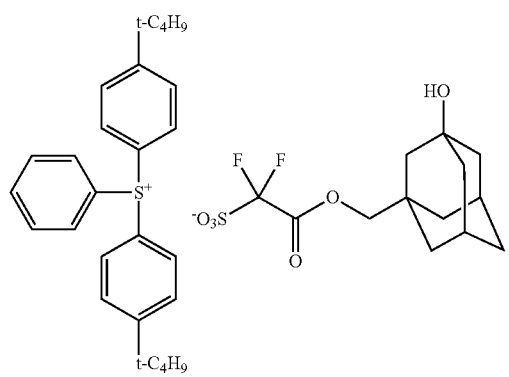
(B1-5)
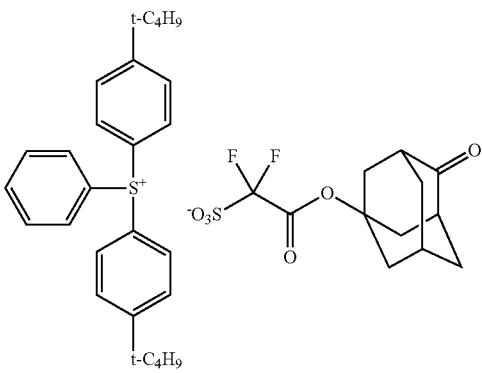
(B1-9)
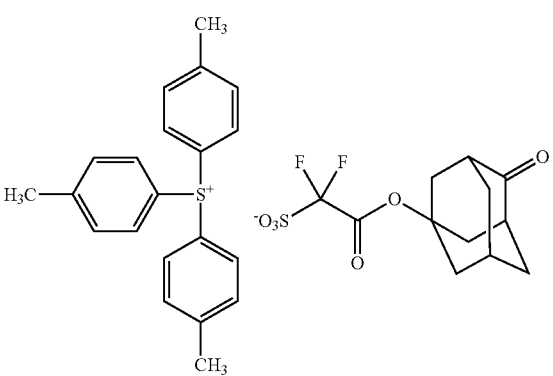
(B1-6)
(B1-7)
(B1-8)
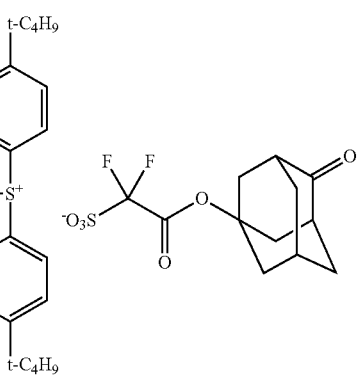
(B1-10)
(B1-11)
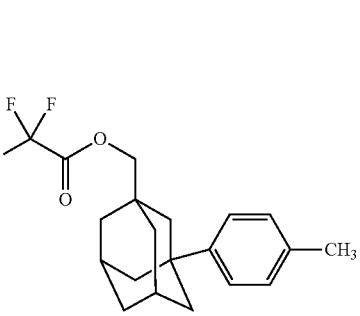
(B1-12)
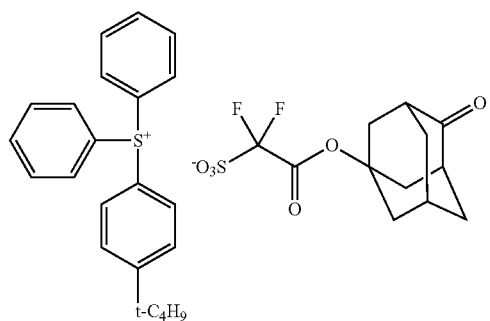
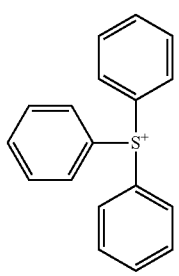

-continued

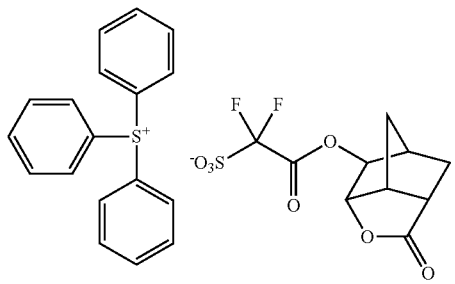
(B1-13)

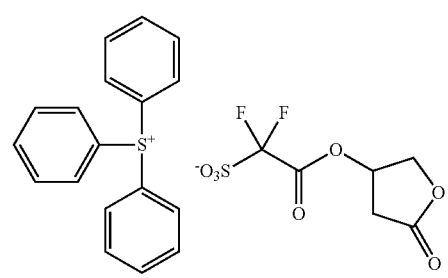
(B1-14)

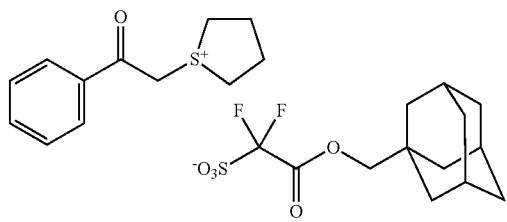
(B1-15)

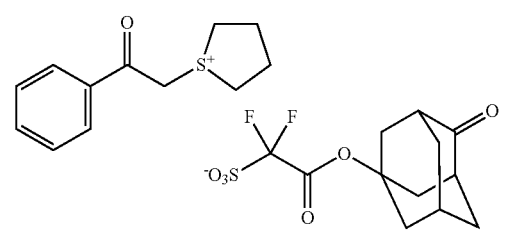
(B1-16)

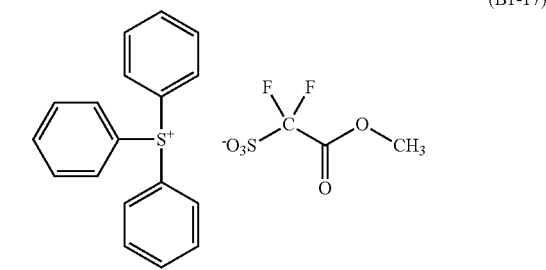
(B1-17)

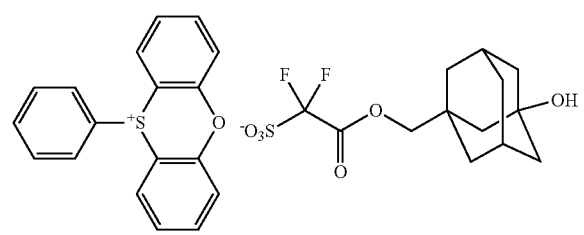
(B1-18)

-continued

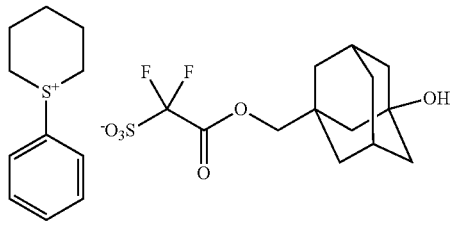
(B1-19)

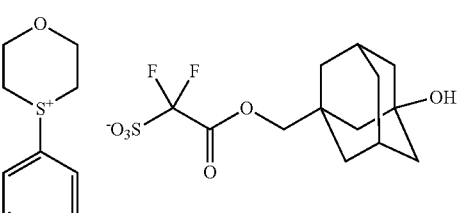
(B1-20)

When an acid generator is only the salt (II) in the photoresist composition, the content of the salt is preferably 1 weight parts or more, more preferably 3 weight parts or more, and preferably 30 weight parts or less, and more preferably 25 weight parts or less relative to 100 weight parts of the total resins.

When an acid generator is the salt (II) and the acid generator other than the salt, the total content of the acid generator is preferably 1 weight parts or more, more preferably 3 weight parts or more, and preferably 40 weight parts or less, and more preferably 35 weight parts or less relative to 100 weight parts of the total resins.

The weight ratio of the salt (II) and the acid generator other than the salt is usually from 5:95 to 95:5, preferably from 10:90 to 90:10, more preferably from 15:85 to 85:15.

The photoresist compositions of the present invention may comprise a compound represented by formula (D):

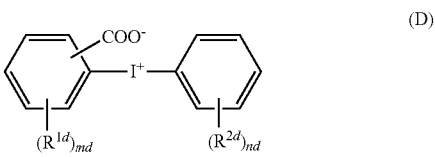
(D)

wherein $R^{1d}$ and $R^{2d}$ each independently represent a C1-C12 hydrocarbon group, a C1-C6 alkoxy group, a C2-C7 acyl group, a C2-C7 acyloxy group, a C2-C7 alkoxycarbonyl group, a nitro group or a halogen atom, and the symbols md and nd each independently represent an integer of 0 to 4.

Examples of the hydrocarbon group represented by $R^{1d}$ and $R^{2d}$ include aliphatic hydrocarbon groups, alicyclic hydrocarbon groups, aromatic hydrocarbon groups and combinations of them.

Examples of the aliphatic hydrocarbon group include alkyl groups such as a methyl group, an ethyl group, a propyl group, isopropyl group, a butyl group, an isobutyl group, t-butyl group, a pentyl group, a hexyl group and a nonyl group.

The alicyclic hydrocarbon groups may be monocyclic or polycyclic which may be saturated and unsaturated. Examples of the aliphatic hydrocarbon group include cycloalkyl groups such as a cyclopropyl group, a cyclobutyl, a cyclopentyl group, a cyclohexyl group, a cyclononyl group and a cyclododecyl group; a norbornyl group; and an adamantyl group.

Examples of aromatic hydrocarbon groups include aryl groups such as a phenyl group, a 1-naphthyl group, a 2-naphthyl group, a 2-methyl phenyl group, a 3-methylphenyl group, a 4-methylphenyl group, a 4-ethylphenyl group, a 4-propylphenyl group, a 4-isopropylphenyl group, a 4-butylphenyl group, 4-t-butyl phenyl group, a 4-hexylphenyl group, a 4-cyclohexylphenyl group, an anthryl group, p-adamantylphenyl group, a tolyl group, a xylyl group, a cumenyl group, a mesityl group, a biphenyl group, a phenanthryl group, a 2,6-diethylphenyl group, 2-methyl-6-ethyphenyl group.

Examples of the combinations of them include alkyl-cycloalkyl groups, cycloalkyl-alkyl groups, and aralkyl groups (e.g., benzyl group, a 1-phenylethyl group, a 2-phenylethyl group, a 1-phenyl-1-propyl group, a 1-phenyl-2-propyl group, a 2-phenyl-2-propyl group, a 3-phenyl-1-propyl group, 4-phenyl-1-butyl group, a 5-phenyl-1-pentyl group, a 6-phenyl-1-hexyl group).

Examples of alkoxy groups include a methoxy group and an ethoxy group.

Examples of acyl groups include an acetyl group, a propanoyl group, a benzoyl group, a cyclohexanecarbonyl group.

Examples of acyloxy group include those in which an oxy group (—O—) has been connected to the acyl group mentioned above.

Examples of alkoxycarbonyl group include those in which a carbonyl group (—CO—) has been connected to an alkoxy group mentioned above.

Examples of halogen atoms include a fluorine atom, a chlorine atom, and a bromine atom.

$R^{1d}$ and $R^{2d}$ each independently represent preferably a C1-C8 alkyl group, a C3-C10 cycloalkyl group, a C1-C6 alkoxy group, a C2-C4 acyl group, a C2-C4 acyloxy group, a C2-C4 alkoxycarbonyl group, a nitro group or a halogen atom.

The symbols md and nd each independently represent preferably an integer of 0 to 2, more preferably 0.

Specific examples of the compound represented by formula (D) include the following ones.

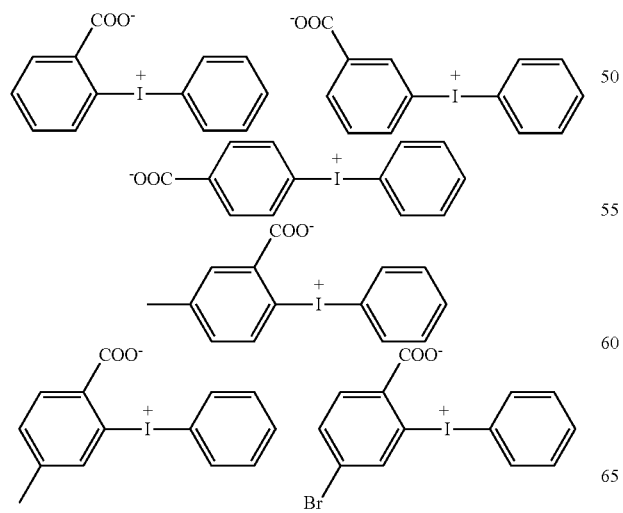

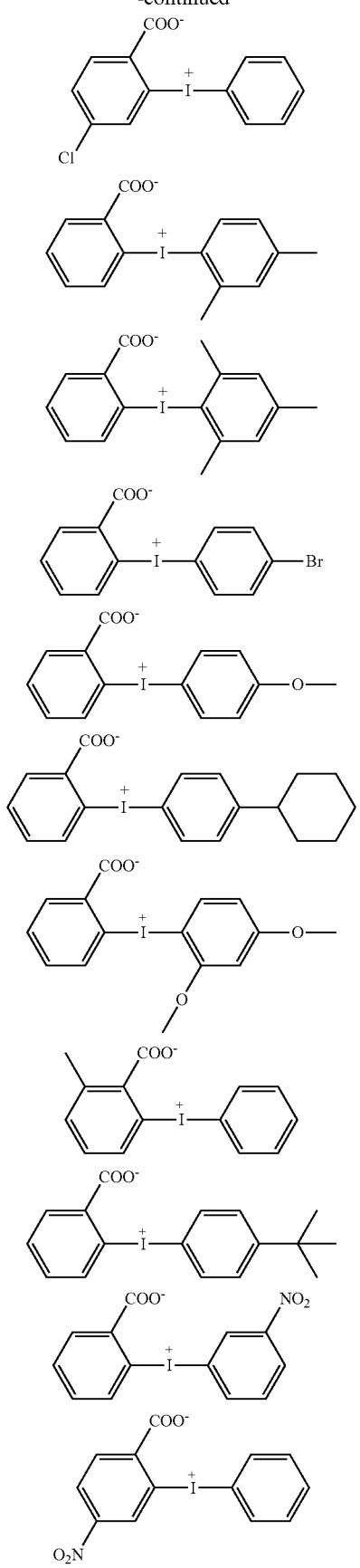

-continued

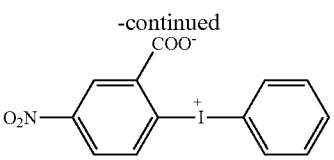

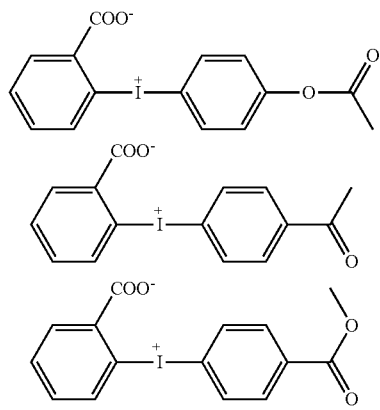

The compound represented by formula (D) can be prepared by the method of mention in "Tetrahedron Vol. 45, No. 19, p 6281-6296", which are commercially available.

The photoresist composition of the present invention comprises usually 0.01% to 5% by weight, preferably 0.01% to 3% by weight, and 0.01% to 1% by weight of the compound represented by formula (D) based on sum of solid component.

The photoresist compositions of the present invention usually contain a solvent.

Examples of the solvent include a glycoletherester such as ethylcellosolve acetate, methylcellosolve acetate and propyleneglycolmonomethylether acetate; an ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The photoresist compositions of the present invention can contain a basic compound.

The basic compound is preferably a basic nitrogen-containing organic compound, and examples thereof include an amine compound and an ammonium salt. Amine compound includes an aliphatic amine and an aromatic amine. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine.

The basic compounds include preferably a compound represented by the formulae (C1), (C2), (C3), (C4), (C5), (C6), (C7) and (C8), more preferably a compound represented by the formulae (C1-1).

wherein $R^{c1}$, $R^{c2}$ and $R^{c3}$ independently represent a hydrogen atom, a C1-C6 alkyl group, a C5-C10 alicyclic hydrocarbon group or a C6-C10 aromatic hydrocarbon group, and the alkyl group and the alicyclic hydrocarbon group can have a substituent selected from the group consisting of a hydroxy group, an amino group and a C1-C6 alkoxy group, and the aromatic hydrocarbon group can have a substituent selected from the group consisting of C1-C6 alkyl groups, a C5-C10 alicyclic hydrocarbon group, a hydroxy group, an amino group, and a C1-C6 alkoxy group,

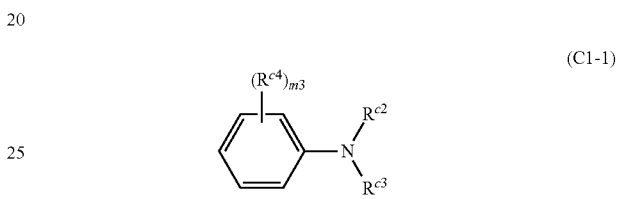

wherein $R^{c2}$ and $R^{c3}$ are defined as above, each of $R^{c4}$ independently represents a C1-C6 alkyl group, a C1-C6 alkoxy group, a C5-C10 alicyclic hydrocarbon group or a C6-C10 aromatic hydrocarbon group, and m3 represents an integer of 0 to 3,

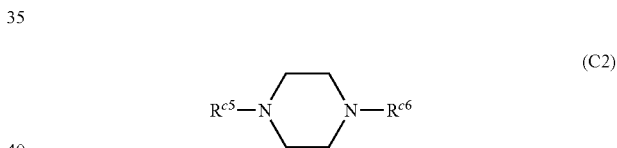

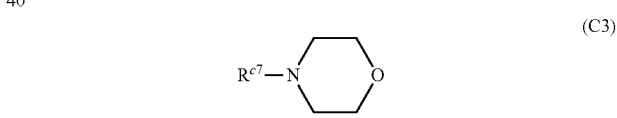

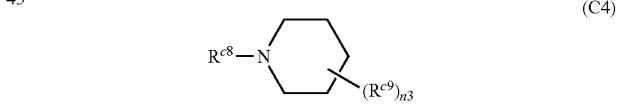

wherein $R^{c5}$, $R^{c6}$, $R^{c7}$ and $R^{c8}$ are defined same as $R^{c1}$, each of $R^{c9}$ independently represents a C1-C6 alkyl group, a C3-C6 alicyclic group, or a C2-C6 alkanoyl group, and n3 represents an integer of 0 to 8,

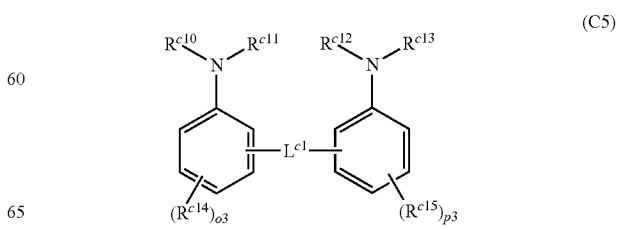

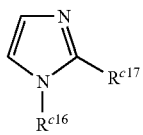
(C6)

wherein each of $R^{c10}$, $R^{c11}$, $R^{c12}$, $R^{c13}$ and $R^{c16}$ is defined same as $R^{c1}$, each of $R^{c14}$, $R^{c15}$ and $R^{c17}$ is defined same as $R^{c4}$,
$L^{c1}$ represents a C1-C6 alkanediyl group, —CO—, —C(=NH)—, —S— or a combination thereof, and o3 and p3 each independently represent an integer of 0 to 3,

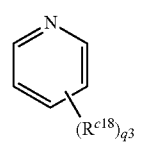
(C7)

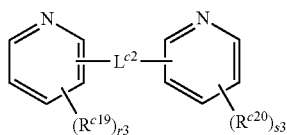
(C8)

wherein each of $R^{c18}$, $R^{c19}$ and $R^{c20}$ is defined same as $R^{c4}$, $L^{c2}$ represents a single bond, a C1-C6 alkanediyl group, —CO—, —C(=NH)—, —S— or a combination thereof, and q3, r3 and p3 each independently represent an integer of 0 to 3.

In each of formulae (C1) to (C8) and formula (C1-1), examples of an alkyl group, an alicyclic hydrocarbon group, an aromatic hydrocarbon group, an alkoxy group and an alkanediyl group are the same as mentioned above.

Examples of alkanoyl groups include an acetyl group, a 2-methyl acetyl group, a 2,2-dimethyl acetyl group, a propionyl group, a butyryl group, an isobutyryl group, a pentanoyl group, a 2,2-dimethyl propionyl group.

Examples of the compound represented by the formula (C1) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, diphenylamine, hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane. Among them, preferred is diisopropylaniline and more preferred is 2,6-diisopropylaniline Examples of the compound represented by the formula (C2) include piperazine.

Examples of the compound represented by the formula (C3) include morpholine.

Examples of the compound represented by the formula (C4) include piperidine and hindered amine compounds having a piperidine skeleton as disclosed in JP11-52575A1.

Examples of the compound represented by the formula (C5) include 2,2'-methylenebisaniline.

Examples of the compound represented by the formula (C6) include imidazole and 4-methylimidazole.

Examples of the compound represented by the formula (C7) include pyridine and 4-methylpyridine.

Examples of the compound represented by the formula (C8) include di-2-pyridylketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine, 2,2'-dipicolylamine and bipyridine.

Examples of the ammonium salt include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 5% by weight, preferably 0.01 to 3% by weight, more preferably 0.01 to 1% by weight based on sum of solid component.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention can usually be prepared by mixing, in a solvent, resin (AI), salt represented by formula (II), and if necessary another resin, another salt, the compound represented by formula (D), a basic compound and/or additives at a suitable ratio for the composition, optionally followed by filtrating the mixture with a filter having 0.03 μm to 0.2 μm of a pore size.

The order of mixing these components is not limited to any specific order. The temperature at mixing the components is usually 10 to 40° C., which can be selected in view of the resin or the like.

The mixing time is usually 0.5 to 24 hours, which can be selected in view of the temperature. The means for mixing the components is not limited to specific one. The components can be mixed by being stirred.

The amounts of the components in the photoresist compositions can be adjusted by selecting the amount to be used for production of them.

The photoresist compositions of the present invention are useful for a chemically amplified photoresist composition.

A photoresist pattern can be produced using the photoresist composition of the present invention by the following steps (1) to (5):

(1) a step of applying the photoresist composition of the present invention on a substrate, (2) a step of forming a composition film by drying the composition, (3) a step of exposing the composition film to radiation, (4) a step of baking the exposed composition film, and (5) a step of developing the baked composition film to form a photoresist pattern.

The applying of the photoresist composition on a substrate is usually conducted using a conventional apparatus such as spin coater. Examples of the substrate include a silicon wafer or a quartz wafer on which a sensor, a circuit, a transistor or the like is formed. The substrate may be coated with a reflect-preventing layer such as one containing hexamethyldisilazane. For forming the reflect-preventing layer, such composition for organic reflect-preventing layer as available on the market can be used.

The composition film is usually formed by heating the coat layer with a heating apparatus such as hot plate or a decompressor, to thereby dry off the solvent. The heating temperature is preferably 50 to 200° C., the time of heating is preferably 10 to 180 seconds, and the operation pressure is preferably 1 to $1.0*10^5$ Pa. These conditions can be selected in view of the solvent.

The composition film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a F2 laser (wavelength: 157 nm), and a light source radiating harmonic laser light in a far UV region or a vacuum UV region by wavelength conversion of laser light from a solid laser light source (such as YAG or semiconductor laser). The exposure source may be electric beam or extremely ultraviolet (EUV).

Exposure through a mask makes the composition film have exposed areas and unexposed area.

The step of baking of the exposed composition film is so called post-exposure bake, which is conducted with heating means such as hot plates. The temperature of baking of the exposed composition film is preferably 50 to 200° C., and more preferably 70 to 150° C. The deprotection reaction further proceeds by post-exposure bake.

The development of the baked composition film is usually carried out with a developer using a development apparatus. The development method includes dipping methods, paddle methods, spray methods and dynamic dispense method. The developing temperature is preferably 5 to 60° C., and the developing time is preferably 5 to 300 seconds.

When a positive type photoresist pattern is prepared from the photoresist composition of the present invention, the development can be conducted with an alkaline developer. The alkaline developer to be used may be any one of various alkaline aqueous solution used in the art. Generally, an aqueous solution of tetramethylammonium hydroxide or (2-hydroxyethyl)trimethylammonium hydroxide (commonly known as "choline") is often used. The alkaline developer may comprise a surfactant.

After development, the composition film having photoresist pattern is preferably washed with ultrapure water, and the remained water on the composition film and the substrate is preferably removed therefrom.

When a negative type photoresist pattern is prepared from the photoresist composition of the present invention, the development can be conducted with a developer containing an organic solvent, such developer is sometimes referred to as "organic developer".

Examples of an organic solvent for organic developer include ketone solvents such as 2-hexanone, 2-heptanone; glycolether ester solvents such as propyleneglycolmonomethylether acetate; ester solvents such as butyl acetate; glycolether solvents such as propyleneglycolmonomethylether; amide solvents such as N,N-dimethylacetamide; and aromatic hydrocarbon solvents such as anisole.

The content of organic solvent is preferably from 90% to 100% by weight, more preferably from 95% to 100% by weight, in an organic developer. Preferred is that the organic developer essentially consists of an organic solvent.

Among them, the organic developer is preferably a developer comprising butyl acetate and/or 2-heptanone.

The total content of butyl acetate and 2-heptanone is preferably from 50% to 100% by weight, more preferably from 90% to 100% by weight. Preferred is that the organic developer essentially consists of butyl acetate and/or 2-heptanone.

The organic developer may comprise a surfactant or a very small amount of water.

Development with an organic developer can be stopped by replacing the developer by other solvents such as alcohol including 4-methyl-2-pentanol and isopropanol.

After development, the photoresist film having a photoresist pattern is preferably washed with a rinse agent. Such agent is not limited to specific one provided that it dissolve the film to be washed, example of which include a solvent containing a general organic solvent, preferably alcohol or ester solvents.

After washing, the remained rinse agent on the photoresist film and the substrate is preferably removed therefrom.

The photoresist composition of the present invention is suitable for KrF excimer laser lithography, ArF excimer laser lithography, EB (electron beam) lithography and EUV exposure lithography, particularly for liquid immersion exposure lithography. The photoresist composition is suitable for the fine processing of the semiconductor.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted.

The weight-average molecular weight of any material used in the following examples is a value found by gel permeation chromatography under the following conditions.

Equipment: HLC-8120GPC type, manufactured by TOSOH CORPORATION

Column: Three of TSKgel Multipore HXL-M with guard column, manufactured by TOSOH CORPORATION Solvent: tetrahydrofuran, Flow rate: 1.0 mL/min.

Detector: RI Detector

Column temperature: 40° C.

Injection volume: 100 μL

Standard reference material: standard polystyrene, manufactured by TOSOH CORPORATION.

The monomers used in the syntheses of the resin are as follow.

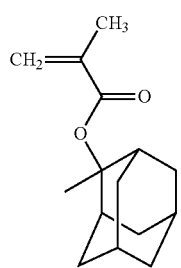 (a1-1-1)
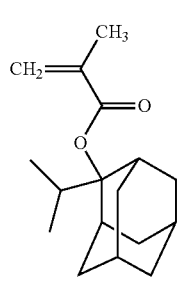 (a1-1-3)
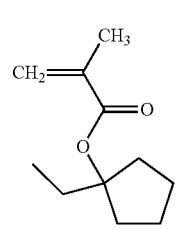 (a1-2-9)
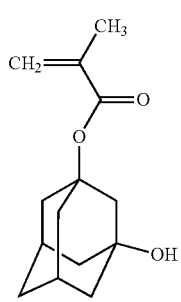 (a2-1-1)
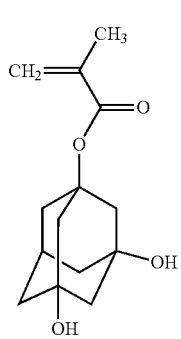 (a2-1-3)
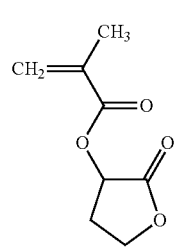 (a3-1-1)
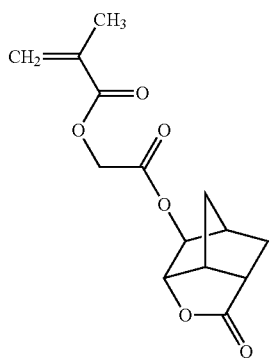 (a3-2-3)
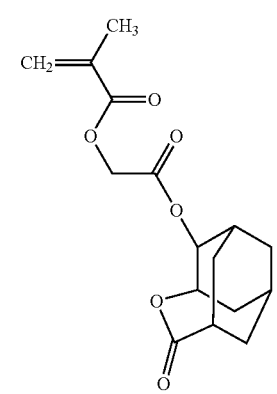 (a4-1)
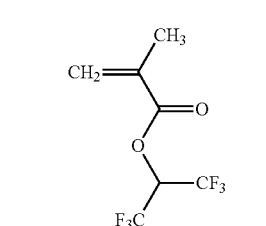 (a4-z)
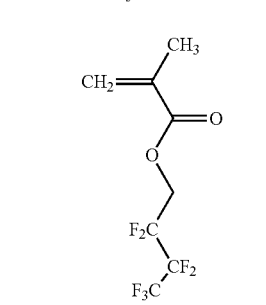 (I-1)
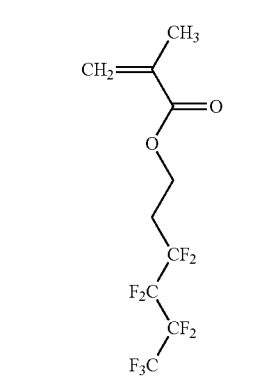 (I-2)

Each monomer is referred to as "monomer X" where X represents the symbol of its formula.

Synthesis Example 1

The monomers (a1-1-3), (a1-2-9), (a2-1-3), (a3-2-3) and (a4-1) were mixed in a molar ratio of 45/14/2.5/22.5/16 (monomer (a1-1-3)/monomer (a1-2-9)/monomer (a2-1-3)/ monomer (a3-2-3)/monomer (a4-1)), and 1,4-dioxane was added thereto in the amount ratio of 1.5 times weight parts relative to the total parts of all monomers to prepare a mixture.

To the mixture, azobisisobutyronitrile as an initiator in the molar ratio of azobisisobutyronitrile/all monomers=1/100 and azobis(2,4-dimethylvaleronitrile) as an initiator in the molar ratio of azobis(2,4-dimethylvaleronitrile)/all monomers=3/100 were added, and the resulting reaction mixture was heated at 73° C. for about 5 hours.

The obtained reaction mixture was poured into a large amount of a mixture of methanol and water to cause precipitation, followed by collecting it by filtration. The precipitate was dissolved in 1,4-dioxane and then poured into a large amount of a mixture of methanol and water to cause precipitation, followed by collecting it by filtration; these steps were conducted twice for purification.

As a result, a resin having a weight-average molecular weight of about $8.8 \times 10^3$ was obtained in a yield of 71%. This resin is called as resin A1. Resin A1 had the following structural units.

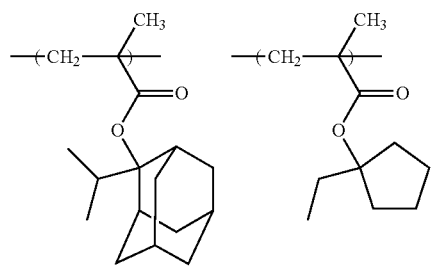

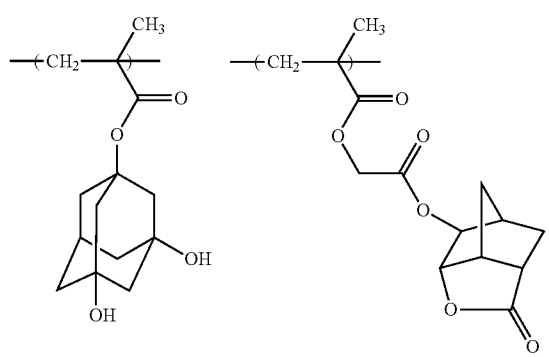

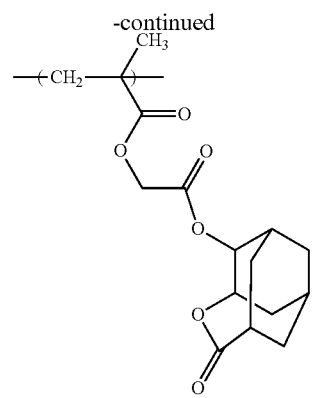

Synthesis Example 2

The monomers (a1-1-3), (a1-2-9), (a2-1-3), (a3-2-1) and (a3-1-1) were mixed in a molar ratio of 45/14/2.5/22/16.5 [monomer (a1-1-3)/monomer (a1-2-9)/monomer (a2-1-3)/ monomer (a3-2-1)/monomer (a3-1-1)], and propyleneglycolmonomethylether acetate was added thereto in the amount ratio of 1.5 times weight parts relative to the total parts of all monomers to prepare a mixture. To the mixture, azobisisobutyronitrile as an initiator in the molar ratio of azobisisobutyronitrile/all monomers=0.95/100, and azobis(2,4-dimethylvaleronitrile) as an initiator in the molar ratio of azobis(2, 4-dimethylvaleronitrile)/all monomers=2.85/100 were added, and the obtained mixture was heated at 73° C. for about 5 hours. The obtained reaction mixture was poured into a large amount of a mixture of methanol and water to cause precipitation, followed by collecting it by filtration. The precipitate was dissolved in propyleneglycolmonomethylether acetate and then poured into a large amount of methanol to cause precipitation, followed by collecting it by filtration; these steps were conducted twice for purification. As a result, a resin having a weight-average molecular weight of about $7.9 \times 10^3$ was obtained in a yield of 73%. This resin is called as resin A2. Resin A2 had the following structural units.

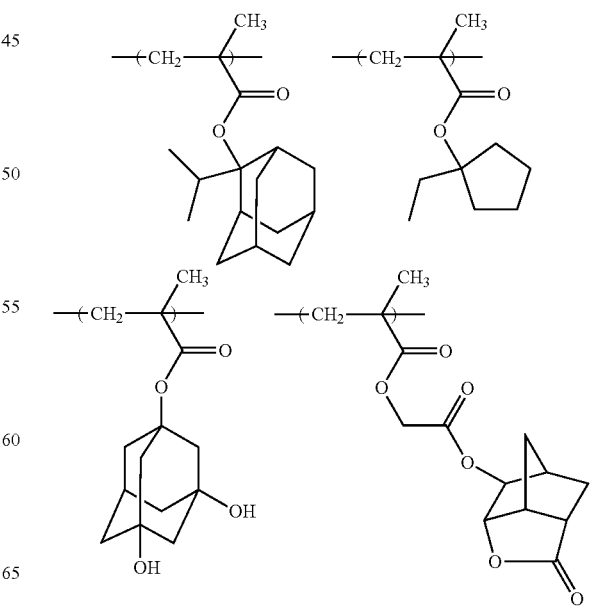

-continued

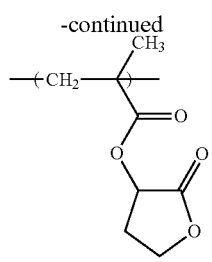

Synthesis Example 3

The monomers (a1-1-1), (a2-1-1) and (a3-1-1) were mixed in a molar ratio of 35/25/40 [monomer (a1-1-1)/monomer (a2-1-1)/monomer (a3-1-1)], and propyleneglycolmonomethylether acetate was added thereto in the amount ratio of 1.5 times weight parts relative to the total parts of all monomers to prepare a mixture. To the mixture, azobisisobutyronitrile as an initiator in the molar ratio of azobisisobutyronitrile/all monomer=1/100 and azobis(2,4-dimethylvaleronitrile) as an initiator in the molar ratio of azobis(2,4-dimethylvaleronitrile)/all monomer=3/100 were added, and the obtained mixture was heated at 75° C. for about 5 hours. The obtained reaction mixture was poured into a large amount of methanol to cause precipitation, followed by collecting it by filtration. The precipitate was dissolved in propyleneglycolmonomethylether acetate and then poured into a large amount of methanol to cause precipitation, followed by collecting it by filtration; these steps were conducted twice for purification.

As a result, a resin having a weight-average molecular weight of about $8.7 \times 10^3$ was obtained in a yield of 90%. This resin is called as resin A3. Resin A3 had the following structural units.

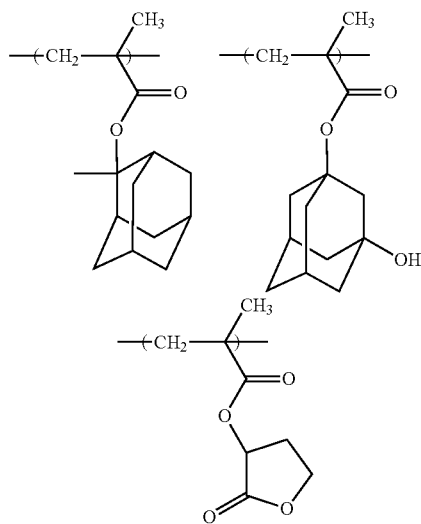

Synthesis Example 4

The monomers (I-1) and (a1-2-9) were mixed in a molar ratio of 50/50 [monomer (I-1)/monomer (a1-2-9)], and methylisobutylketone was added thereto in the amount ratio of 1.2 times weight parts relative to the total parts of all monomers to prepare a mixture.

To the mixture, azobis(2,4-dimethylvaleronitrile) as an initiator in the molar ratio of azobis(2,4-dimethylvaleronitrile)/all monomers=3/100 were added, and the obtained mixture was heated at 70° C. for about 5 hours.

The obtained reaction mixture was poured into a large amount of a mixture of methanol and water to cause precipitation, followed by collecting it by filtration. The precipitate was dissolved in propyleneglycolmonomethylether acetate and then poured into a large amount of a mixture of methanol and water to cause precipitation, followed by collecting it by filtration; these steps were conducted twice for purification. As a result, a resin having a weight-average molecular weight of about $9.0 \times 10^3$ was obtained in a yield of 85%.

This resin is called as resin H1. Resin H1 had the following structural units.

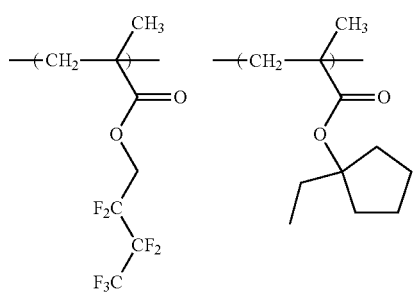

Synthesis Example 5

To monomer (a4-z), propyleneglycolmonomethylether acetate was added in the amount ratio of 4 times weight parts relative to the total parts of the monomer to prepare a mixture. To the mixture, V-601 (WAKO PURE CHEMICAL) as an initiator in the molar ratio of V-601/the monomer=8/100 was added, and the obtained mixture was heated at 80° C. for about 5 hours. The obtained reaction mixture was poured into a large amount of a mixture of methanol and water to cause precipitation, followed by collecting it by filtration. The precipitate was dissolved in propyleneglycolmonomethylether acetate and then poured into a large amount of a mixture of methanol and water to cause precipitation, followed by collecting it by filtration; these steps were conducted twice for purification. As a result, a resin having a weight-average molecular weight of about $7.6 \times 10^3$ was obtained in a yield of 70%. This resin is called as resin H2.

Resin H2 had the following structural unit.

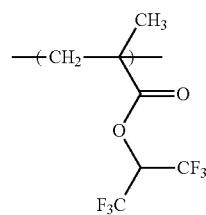

Synthesis Example 6

The monomers (I-2) and (a1-2-9) were mixed in a molar ratio of 50/50 [monomer (I-2)/monomer (a1-2-9)], and methylisobutylketone was added thereto in the amount ratio of 1.2 times weight parts relative to the total parts of all monomers to prepare a mixture.

To the mixture, azobis(2,4-dimethylvaleronitrile) as an initiator in the molar ratio of azobis(2,4-dimethylvaleronitrile)/all monomers=3/100 were added, and the obtained mixture was heated at 70° C. for about 5 hours.

The obtained reaction mixture was poured into a large amount of a mixture of methanol and water to cause precipitation, followed by collecting it by filtration. The precipitate was dissolved in propyleneglycolmonomethylether acetate and then poured into a large amount of a mixture of methanol and water to cause precipitation, followed by collecting it by filtration; these steps were conducted twice for purification. As a result, a resin having a weight-average molecular weight of about $9.1 \times 10^3$ was obtained in a yield of 87%.

This resin is called as resin H3. Resin H3 had the following structural units.

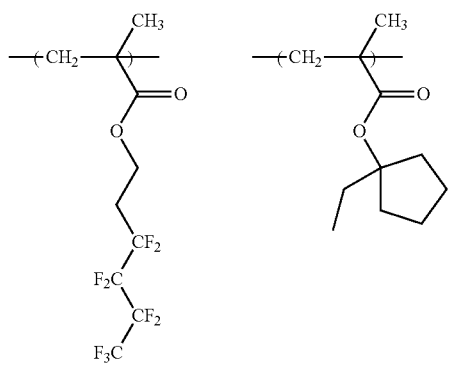

Synthesis Example 7

The monomers (I-1) and (a1-1-1) were mixed in a molar ratio of 50/50 [monomer (I-1)/monomer (a1-1-1)], and methylisobutylketone was added thereto in the amount ratio of 1.2 times weight parts relative to the total parts of all monomers to prepare a mixture.

To the mixture, azobis(2,4-dimethylvaleronitrile) as an initiator in the molar ratio of azobis(2,4-dimethylvaleronitrile)/all monomers=3/100 were added, and the obtained mixture was heated at 70° C. for about 5 hours. The obtained reaction mixture was poured into a large amount of a mixture of methanol and water to cause precipitation, followed by collecting it by filtration.

The precipitate was dissolved in propyleneglycolmonomethylether acetate and then poured into a large amount of a mixture of methanol and water to cause precipitation, followed by collecting it by filtration; these steps were conducted twice for purification.

As a result, a resin having a weight-average molecular weight of about $9.4 \times 10^3$ was obtained in a yield of 83%. This resin is called as resin H4. Resin H4 had the following structural units.

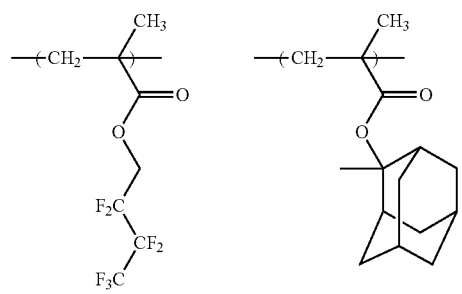

Examples 1 to 10 and Comparative Examples 1 to 2

Preparation of Photoresist Composition

The following components shown in Table 1 were mixed and dissolved, further, filtrated through a fluorine resin filter having pore diameter of 0.2 μm, to prepare photoresist compositions.

TABLE 1

| No. | Resin (Kind/Parts) | Acid generator (Kind/Parts) | Compound (Kind/Parts) | Quencher (Kind/Parts) | PB/PEB |
|---|---|---|---|---|---|
| Composition 1 | H1/0.5 A1/10 | I1-2/0.4 B1-3/0.4 | D1/0.35 | None | 100° C./90° C. |
| Composition 2 | H1/0.2 A2/10 | I1-2/0.4 B1-3/0.4 | D1/0.35 | None | 100° C./90° C. |
| Composition 3 | H1/0.5 A2/10 | I1-2/0.4 B1-3/0.4 | D1/0.35 | None | 100° C./90° C. |
| Composition 4 | H1/0.8 A2/10 | I1-2/0.4 B1-3/0.4 | D1/0.35 | None | 100° C./90° C. |
| Composition 5 | H1/1.2 A2/10 | I1-2/0.4 B1-3/0.4 | D1/0.35 | None | 100° C./90° C. |
| Composition 6 | H1/2 A2/10 | I1-2/0.4 B1-3/0.4 | D1/0.35 | None | 100° C./90° C. |
| Composition 7 | H2/0.5 A2/10 | I1-2/0.4 B1-3/0.4 | D1/0.35 | None | 100° C./90° C. |
| Composition 8 | H3/0.5 A2/10 | I1-2/0.4 B1-3/0.4 | D1/0.35 | None | 100° C./90° C. |
| Composition 9 | H4/0.5 A1/10 | I1-2/0.4 B1-3/0.4 | D1/0.35 | None | 100° C./90° C. |
| Composition 10 | H4/0.5 A2/10 | I1-2/0.4 B1-3/0.4 | D1/0.35 | None | 100° C./90° C. |
| Compar. Composition. 1 | H2/0.5 A3/10 | Z1/0.685 | None | C1/0.08 | 120° C./120° C. |

The symbols shown in Table 1 represent the following components.

<Resin>

A1: Resin A1, A2: Resin A2, A3: Resin A3,

H1: Resin H1, H2: Resin H2, H3: Resin H3, H4: Resin H4

<Acid Generator>

I1: Salt represented by formula (I1-2), manufactured by Central Grass, Ltd.

B1-3: Salt represented by formula (B1-3), prepared in a manner described in Examples of JP2010-152341A1

Z1: Salt represented by formula (Z1)

<Quencher>
C1: 2,6-diisopropylaniline (Product of Tokyo Chemical Industry, Co., Ltd.)
<Compound Represented by Formula (D)>
D1: The compound represented by the following formula <Solvent>

| propylene glycol monomethyl ether acetate | 250 parts |
| propylene glycol monomethyl ether | 20 parts |
| 2-heptanone | 20 parts |
| γ-butyrolactone | 3.5 parts |

Production of Photoresist Pattern

Silicon wafers (12 inches) were each coated with "ARC-29", which is an organic anti-reflective coating composition available from Nissan Chemical Industries, Ltd., and then baked at 205° C. for 60 seconds, to form a 78 nm-thick organic anti-reflective coating.

Each of the photoresist compositions prepared as above was spin-coated over the anti-reflective coating so that the thickness of the resulting film became 110 nm after drying.

The silicon wafers thus coated with the respective photoresist compositions were each prebaked on a direct hotplate at a temperature shown in the column "PB" in Table 1 for 60 seconds.

Using an ArF excimer stepper for immersion exposure ("XT: 1900Gi" manufactured by ASML, NA=1.35, ¾ Annular, X-Y polarization) and a mask for contact-hole pattern (hole pitch 120 nm/diameter of hole 55 nm), each wafer thus formed with the respective composition film was subjected to the exposure with the exposure quantity being varied stepwise. Ultra pure water was used for immersion solvent.

After the exposure, each wafer was subjected to post-exposure baking on a hotplate at a temperature shown in the column "PEB" in Table 1 for 60 seconds and then to conduct development in the manner of dynamic dispense method for 20 seconds at 23° C. with butyl acetate, product of Tokyo Chemical Industry, Co., Ltd.

<Evaluation of Resolution>

Each of negative photoresist patterns after the development was observed with a scanning electron microscope.

When the pattern with diameter 55 nm was free from a plugged portion, the composition having such pattern is evaluated as good and marked by "○" in Table 2. When the pattern with diameter 55 nm had a plugged portion, the composition having such pattern is evaluated as bad and marked by "X" in Table 2.

Effective sensibility (ES) means the exposure quantity such that the diameter of hole pattern became 55 nm after exposure through the above-mentioned mask.

<Evaluation of Focus Margin (DOF)>

The photoresist patterns were obtained at the exposure amount of ES, with the focal point distance being varied stepwise.

Each of patterns developed on the organic anti-reflective coating substrate after the development were observed and the focal point distances when the patterns of which hole diameter were within 55 nm±5% (from 60.5 nm and 49.5 nm) were measured and the difference between the max value of the focal point distance and the minimum value of the focal point distance was calculated. Each of the differences is also shown in parentheses in a column of "DOF". The difference is bigger, the better focus margin the photoresist composition has.

<Evaluation of CD Uniformity (CDU)>

The photoresist patterns were prepared in the same manner as mentioned above except that a mask forming contact-hole pattern (hole pitch 120 nm/diameter of hole 60 nm) was used.

The photoresist patterns were observed with a scanning electron microscope. The hole diameter of the contact hole pattern was twenty four (24) times measured and its average diameter was calculated.

The average diameters of 105 holes on the same wafer were respectively measured. Defining the average diameters of 105 holes as its population, the standard deviation was calculated as CDU. The smaller the standard deviation is, the better is. Further, each of CDU is shown in columns of "CDU" of Table 2.

TABLE 2

| Ex. No. | Composition | Resolution | ES (mJ/cm$^2$) | DOF (nm) | CDU (nm) |
|---|---|---|---|---|---|
| Ex. 1 | Composition 1 | ○ | 14.3 | 80 | 2.0 |
| Ex. 2 | Composition 2 | ○ | 14.9 | 90 | 2.0 |
| Ex. 3 | Composition 3 | ○ | 14.8 | 90 | 2.0 |
| Ex. 4 | Composition 4 | ○ | 14.9 | 90 | 1.9 |
| Ex. 5 | Composition 5 | ○ | 14.9 | 100 | 1.9 |
| Ex. 6 | Composition 6 | ○ | 14.8 | 100 | 1.8 |
| Ex. 7 | Composition 7 | ○ | 14.6 | 50 | 2.6 |
| Ex. 8 | Composition 8 | ○ | 14.3 | 80 | 2.0 |
| Ex. 9 | Composition 9 | ○ | 14.1 | 80 | 1.9 |
| Ex. 10 | Composition 10 | ○ | 14.6 | 90 | 1.9 |
| Compar. Ex. 1 | Comparative Composition 1 | X | — | — | — |

The photoresist composition of the present invention can provide a good photoresist pattern with excellent pattern profile.

What is claimed is:

1. A photoresist composition comprising
a resin which comprises a structural unit represented by formula (I):

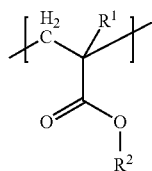

(I)

wherein $R^1$ represents a hydrogen atom or a methyl group, and
$R^2$ represents a C1-C10 saturated hydrocarbon group having a fluorine atom; and
a resin which comprises a structural unit having an acid-labile group and no structural unit represented by formula (I); and
an acid generator represented by formula (IIA)

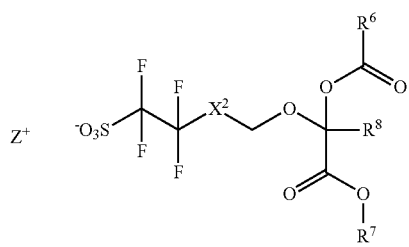

(IIA)

wherein $X^2$ represents a C1-C6 alkanediyl group where a hydrogen atom can be replaced by a hydroxyl group or a group —O—$R^5$ and where a methylene group can be replaced by an oxygen atom or a carbonyl group,
$R^5$ represents a C1-C24 hydrocarbon group where a hydrogen atom can be replaced by a fluorine atom or a hydroxyl group and where a methylene group can be replaced by an oxygen atom or a carbonyl group,
$R^6$ represent a C1-C17 hydrocarbon group where a hydrogen atom can be replaced by a fluorine atom or a hydroxyl group and where a methylene group can be replaced by an oxygen atom or a carbonyl group,
$R^7$ represents a C1-C6 alkyl group,
$R^8$ represents a C1-C6 fluoroalkyl group, provided that the total number of carbon atoms in $R^6$, $R^7$ and $R^8$ is 19 or less, and
$Z^+$ represents an organic cation.

2. The photoresist composition according to claim 1, which further comprises a salt represented by formula (B1):

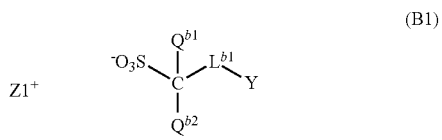

(B1)

wherein $Q^{b1}$ and $Q^{b2}$ each independently represent a fluorine atom or a C1-C6 perfluoroalkyl group,
$L^{b1}$ represents a single bond or a C1-C17 divalent saturated hydrocarbon group where a methylene group can be replaced by an oxygen atom or a carbonyl group,
Y represents a hydrogen atom or a C3-C18 alicyclic hydrocarbon group where a methylene group can be replaced by an oxygen atom, a sulfonyl group or a carbonyl group and where a hydrogen atom can be replaced by a substituent, and
$Z1^+$ represents an organic cation.

3. The photoresist composition according to claim 1, which further comprises a compound represented by formula (D):

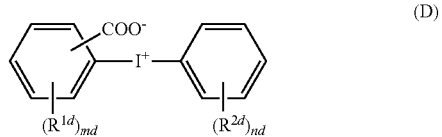

(D)

wherein $R^{1d}$ and $R^{2d}$ each independently represent a C1-C12 hydrocarbon group, a C1-C6 alkoxy group, a C2-C7 acyl group, a C2-C7 acyloxy group, a C2-C7 alkoxycarbonyl group, a nitro group or a halogen atom, and the symbols md and nd each independently represent an integer of 0 to 4.

4. The photoresist composition according to claim 1, wherein the structural unit represented by formula (I) is one represented by formula (Ia)

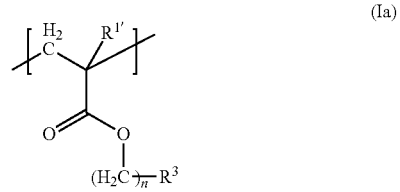

(Ia)

where $R^1$ represents a hydrogen atom or a methyl group,
$R^3$ represents a C1-C4 perfluoroalkyl group, and
n represents an integer of 1 to 4.

5. The photoresist composition according to claim 1, which further comprises a solvent.

6. A process for producing a photoresist pattern comprising the following steps (1) to (5):
   (1) a step of applying the photoresist composition according to claim 1 on a substrate,
   (2) a step of forming a composition film by drying the composition,
   (3) a step of exposing the composition film to radiation,
   (4) a step of baking the exposed composition film, and
   (5) a step of developing the baked composition film, thereby forming a photoresist pattern.

* * * * *